United States Patent
Alsaloum

(10) Patent No.: US 11,135,276 B2
(45) Date of Patent: Oct. 5, 2021

(54) METHOD OF MAKING PDIA2 AND COMPOSITIONS CONTAINING PDIA2

(71) Applicant: Imam Abdulrahman Bin Faisal University, Dammam (SA)

(72) Inventor: Manal Abdullah Alsaloum, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 48 days.

(21) Appl. No.: 16/415,413

(22) Filed: May 17, 2019

(65) Prior Publication Data

US 2020/0360494 A1    Nov. 19, 2020

(51) Int. Cl.
*A61K 38/52*    (2006.01)
*C12N 9/90*    (2006.01)
*C12N 9/10*    (2006.01)
*A61K 9/06*    (2006.01)

(52) U.S. Cl.
CPC ............... *A61K 38/52* (2013.01); *A61K 9/06* (2013.01); *C12N 9/1088* (2013.01); *C12N 9/90* (2013.01); *C12Y 503/04001* (2013.01); C07K 2319/23 (2013.01)

(58) Field of Classification Search
None
See application file for complete search history.

(56) References Cited

FOREIGN PATENT DOCUMENTS

| CN | 1995343 A | 7/2007 |
|---|---|---|
| JP | 2018033347 A | 3/2018 |
| WO | 2014/138371 A1 | 9/2014 |

OTHER PUBLICATIONS

Kurisaki, et al. ; Autoimmune Gastro-Pancreatitis with Anti-Protein Disulfide Isomerase-Associated 2 Autoantibody in Aire-Deficient BALB/cAnN Mice ; Plos One ; vol. 8, Issue 8 ; Aug. 2013 ; 8 Pages.
Walker, et al. ; N-linked glycosylation modulates dimerization of protein disulfide isomerase family A member 2 (PDIA2) ; FEBS Journal 280 ; pp. 233-243 ; 2013 ; 11 Pages.

*Primary Examiner* — David W Berke-Schlessel
(74) *Attorney, Agent, or Firm* — Oblon, McClelland, Maier & Neustadt, L.L.P.

(57) ABSTRACT

A method for producing soluble PDIA2, compositions containing it, and methods for its use.

20 Claims, 12 Drawing Sheets
Specification includes a Sequence Listing.

FIG. 1A

| Name | Length | Domains a b b' a' | Number of thioredoxin-like domains | ER localization motif |
|---|---|---|---|---|
| PDI | 508 | | 4 | KDEL |
| PDIA2 | 525 | | 4 | KEEL |
| ERP57 | 505 | | 4 | QEDL |
| ERP72 | 645 | | 5 | KEEL |
| ERdj5 | 793 | | 6 | KDEL |
| PDILT | 584 | | 4 | KEEL |
| PDIr | 519 | | 4 | KEEL |
| P5 | 440 | | 3 | KDEL |
| ERp44 | 406 | | 3 | RDEL |
| Erp29 | 261 | | 1 | KEEL |
| ERp27 | 273 | | 2 | KVEL |
| ERp18 | 172 | | 1 | EDEL |
| ERp46 | 432 | | 3 | KDEL |
| TMX | 280 | | 1 | Unknown |
| TMX2 | 296 | | 1 | KKDK |
| TMX3 | 454 | | 3 | KKDK |
| TMX4 | 349 | | 1 | RQR |
| TMX5 | 330 | | 1 | KKDK |
| Hag-2 | 175 | | 1 | KTEL |
| Hag-3 | 165 | | 1 | QSEL |

METHOD OF MAKING PDIA2 AND COMPOSITIONS CONTAINING PDIA2

REFERENCE TO A SEQUENCE LISTING

In accordance with 37 CFR § 1.52(e)(5), the present specification makes reference to a Sequence Listing which is submitted electronically as a .txt file named "518852US_Sequence_Listing_ST25.txt". The .txt file was generated on May 15, 2019 and is 12.7 kb in size. The entire contents of the Sequence Listing are herein incorporated by reference.

BACKGROUND OF THE INVENTION

Field of the Invention

This application pertains to the fields of medicine and molecular biology.

Description of Related Art

The protein disulfide isomerase (PDI) family plays a significant role in catalyzing protein folding and exhibits chaperonin activity. The family of protein disulphide isomerase (PDIs) includes multifunctional proteins, mainly located in the lumen of the endoplasmic reticulum (ER). Various organisms express different families of PDI, some of them, such as yeast $PDI1_p$ and human PDI are similar, whereas many other organisms have a unique set of PDIs. The human PDI family comprises at least 20 members. Most of the human PDIs have at least one thioredoxin-like domain which is similar to one of the four domains of other PDI members (EC 5.3.4.1; see hypertext transfer protocol secure at brenda-enzymes.org/enzyme.php?ecno=5.3.4.1; last accessed Apr. 19, 2019, incorporated by reference). Consistent with this observation, these members are defined by their similarity to PDI member domains and localization in the ER rather than their functions. PDI was acknowledged as a member of the thioredoxin superfamily due to the significant sequence identity between the PDI domain and thioredoxin protein. However, the thioredoxin-like domain function can vary as it can be catalytic because of one or two active-site cysteines or non-catalytic. The cysteines in PDI active sites are thought to be crucial for its enzymatic activity.

PDIA2 is a lesser known member of the PDI family. While it is known that PDIA2 plays a significant role in some diseases such as pancreatic cancer and neurodegenerative disease, comparatively little is known about its cellular activities and roles.

PDI Structure. The PDI protein structure includes both catalytic and non-catalytic domains. A PDI protein can be divided into four parts: catalytic domains (a, a'), non-catalytic domains (b, b'), an x-linker region between b' and a' domains, and a small C-terminal domain (c). Sequence homologies exist between the (a, a') domains and the thioredoxin domain. Hence, the (a, a') domains are known as a thioredoxin-like catalytic domain and each of these domains has two cysteine residues in the active site with an intervening GH sequence (—CGHC—). The active site motif is involved in thiol-disulfide reactions making it crucial for PDI enzymatic activity.

Surprisingly, the b and b' domains also have a thioredoxin-like structure but they lack cysteine residues and thus are characterized as non-catalytic domains. The b' domain is the major binding site for substrates, however other domains are involved in the binding of protein. FIG. 1A depicts the structures of some members of the PDI family, including PDIA2 (second entry). The full length crystal structures of other PDIs members, such as ERp29 and ER57 in complex with tapasin, have been identified which will facilitate identifying structure and function relationships.

PDI Function. The biogenesis of approximately a third of human protein requires the formation of disulfide bonds. PDIs play a major role in this crucial process. The name of this protein family may indicate that all members participate in protein disulphide isomerization. However, it has been demonstrated that not all members have this particular enzymatic activity. PDI members with only one cysteine in the active site, such as Hag2 and Hag3 have a poor oxidoreductase activity; Persson et al., 2005. In addition, the PDI family includes non-catalytic members such as ERp27 and ERp29; Van Lith et al., 2007. Several studies have found that PDI catalyzes the oxidation, reduction and rearrangement of disulfide bonds (Darby & Creighton, 1995). Moreover, it has been shown that PDI can exhibit a molecular chaperone and anti-chaperone activity; Wang & Tsou, 1993; Quan et al., 1995.

A number of activities can be regulated by extracellular PDIs, such as pathogen entry like human immunodeficiency virus (HIV), cellular adhesion and blood platelet aggregation and secretion. Furthermore, PDIs are involved in cardiovascular disease and cancer immune recognition. Some PDIs play a protective role against protein aggregation and thus can modulate neurodegenerative diseases, such as amyotrophic lateral sclerosis which can result from an accumulation of aggregated protein.

An accumulation of misfolded and aggregated protein in affected tissue are hallmarks of ALS. The majority of ALS cases are sporadic (sALS), without any family history of the disease—only about 10% of cases have previous family history of ALS, now termed familial ALS (fALS). The peak age for developing the sporadic disease is 58-63 years whereas, the peak age for developing the familial disease is 47-52 years. Interestingly, inherited mutation in superoxide dismutase 1 (SOD1) caused 20% of (fALS) cases.

Superoxide Dismutases. Superoxide dismutases (SODs) are a group of enzymes, which are characterized by their function to dismute $O_2^-$ and by the metals they contain. SOD1 exhibits antioxidant activity by catalyzing the reduction of superoxide radicals into hydrogen peroxide and di-oxygen. This reduces the steady state concentration of superoxide radicals in an organism.

SOD1, a copper and zinc form of SOD (Cu—Zn SOD), is one of three human superoxide dismutases and has a molecular mass of 32 kDa. Normally, wild type SOD1 is located in the cytoplasm with little being present in the nucleus, mitochondrial inter-membrane space, outer membrane peroxisomes or matrix. Mutations, such as single residue point mutations, in SOD1, have been associated with aggregation of SOD1 and with ALS. Aggregated SOD1 may improperly fold or become sticky to itself or to other proteins and aggregate. The crystal structure of SOD1 has been solved with a copper ion on one chain and a zinc metal ion on the other; see FIG. 1B. These metal binding sites are crucial for the stability and catalytic activity of the protein.

Human SOD1 has four cysteine residues. Residues Cys-57 and Cys-146 are linked by a conserved intra-subunit disulfide bond that stabilizes the protein. Residues Cys-6 and Cys-111 are not linked with disulfide bond under normal conditions; Cozzolino et al., 2008—incorporated herein by reference in its entirety. More than 150 different SOD1 gene mutations have been identified in ALS patients most of which with autosomal dominant transmission. SOD1 missense variants include: A4V, G37R, L38V, G41S, G41D, H43R, G85R, G93A, G93C, E100G, L106V, I113T, L144F, and V148G. Some of missense variants associated with SOD1 ALS such as H46R, H48Q, G85R, D124V, D125H, S134N have reduced superoxide dismutase activity, but others such as A4V, L38V, G37R, G41S, G72S, D76Y, D90A, G93A, and ΔE133 retain full enzymatic activity.

PDIA2 involvement in disease. Laboratory studies indicate that mutations in the PDIA2 could be the cause of bicuspid aortic valve (BAV) which is an extremely common heredity heart defect. However, in some haplotypes BAV is also linked with axis inhibitor 1 (AXIN1) so it is difficult to speculate the crucial role of PDIA2 in BAV, whereas the role of PDIA2 in heart disease is unknown. PDIA2 may be a protective factor to combat the development of pancreatic cancer in humans. Pancreatic cancers are a very common in males compared to females suggesting a negative association between estrogenic status of a subject and the progression of pancreatic cancers. It has been shown that PDIA2 can function as an intracellular estrogen binding protein and as a result can affect the physiological function of estrogen in the pancreas.

Having recognized the potential importance of PDIA2 for therapeutic and diagnostic use the inventors sought to provide a convenient method and system to purify PDIA2 in a soluble and active form that could be used therapeutically to help refold denatured or damage proteins and to treat damaged tissues.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings. The invention includes but is not limited to the following embodiments.

One embodiment of the invention is a method for treating damaged tissue comprising contacting the damaged tissue with soluble PDIA2. Such a tissue may constitute the skin or a mucous membrane to which PDIA2 can be applied topically. Lacerated or abraded skin, sunburned skin, skin exposed to environmental toxins, such as estrogen-like contaminants, or irritants, or skin subject to other forms of dermatitis, may be treated by topical application of a PDIA2 composition. Alternatively, tissues inside the body such as inside the mouth or along the gastrointestinal tract lining may be treated by oral administration of a PDIA2 composition which in some embodiments, is prepared in a form that permits passage of PDIA2 through the stomach into the intestine, such as in an encapsulated form. In some embodiments, a sterile PDIA2 composition may be parenterally administered to a subject, for example, by injection under the skin, into a muscle, into the circulatory system or into a target tissue or organ, such as into the pancreas or other organ in need of PDIA2. PDIA2 may be conjugated or complexed with cell penetrating peptides to enhance its entry into cell; see CopolOvici, et al., *ACS Nano*, 2014, 8 (3), pp 1972-1994; DOI: 10.1021/nn4057269; Milletti, Francesca (2012). "*Cell-penetrating peptides: Classes, origin, and current landscape*". *Drug Discovery Today*. 17 (15-16): 850-860; Stalmans, S., et al. (2013). "*Chemical-Functional Diversity in Cell-Penetrating Peptides*". *PLOS ONE*. 8 (8): e71752; Wagstaff K. et al., (2006). "*Protein Transduction: Cell Penetrating Peptides and Their Therapeutic Applications*". *Current Medicinal Chemistry*. 13 (12): 1371-1387. doi:10.2174/092986706776872871, each incorporated by reference.

Soluble PDIA2 may be administered to subjects having diseases, disorders or conditions characterized by protein aggregation, such as the aggregation of SOD1. Such diseases, disorders or conditions include neurodegenerative diseases, such as amyotrophic lateral sclerosis which can result from an accumulation of aggregated protein In some embodiments this method of treatment is performed using a composition that comprises, consists essentially of, or consists of PDIA2, a PDIA2 fusion protein, such as GST-PDIA2, or a PDIA2 variant, such as one having at least 90% sequence identity to the PDIA2 sequence of SEQ ID NO: 2. In other embodiments, the method may be performed using a PDIA2 composition that contains other active ingredients such as an antioxidant or superoxide dismutase.

In some embodiments, this method of treatment is performed using a composition in which the PDIA2 is produced by recombinant expression of a DNA construct in a prokaryotic or eukaryotic host cell. A preferred host cell is *Escherichia coli*. More preferably, the host cell will be *E.coli* that contains tRNA genes, such as 1, 2, 3 or more extra tRNA genes for amino acid codons found in human genes encoding PDIA2, for example, it may contain extra copies of the argU, ileY, and leuW tRNA genes.

In some embodiments, the host cells is selected or engineered so as to not form disulfide bonds within the expressed PDIA2. For example, the *E. coli* used to express PDIA2 for use in the method disclosed above may contain deletions of genes that prevent expression and recovery of soluble PDIA2, such a deletion of one or more disulfide bond isomerase proteins such as DsbC.

The expression of a PDIA2 or PDIA2 fusion protein for use in the method above may be induced, for example, by contacting host cells transformed with DNA encoding PDIA2 or a PDIA2 fusion protein with isopropyl β-D-1-thiogalactopyranoside (IPTG), for example, with a concentration of IPTG ranging from 0.01, 0.05, 0.1, 0.2, 0.3, 0.4, 0.5, 1.0 or >1.0 mM. Preferably, no more than 0.1 mM concentration of IPTG is used.

Induction or expression of a soluble recombinant PDIA2 protein in *E. coli* or other host cell is advantageously performed at a low temperature, such as a temperature no more than 40, 37, 35, 30, 25, 20, 19, 18, 17, 16, 15, 14, 13, 12, 11, 10° C. While not being bound to any particular theory or explanation, the inventor believes that PDIA2, which can bind to and interact with other cellular proteins, binds to other cellular proteins to a lesser degree at low temperatures.

Another embodiment of the invention is directed to a method for making soluble PDIA2 which includes (a) inducing expression of a GST-PDIA2 fusion protein, which comprises a glutathione-S-transferase (GST) tag and a segment of PDIA2 having disulphide isomerase activity, in host cells, which contain nucleic acids encoding said fusion protein, at no more than 30° C., (b) disrupting the host cells containing the expressed GST-PDIA2 fusion protein; (c) separating the disrupted host cells into solid and soluble fraction; and (d) recovering GST-PDIA2 fusion protein from the soluble fraction. In some alternative embodiments, tags other than GST may be fused to PDIA2, active fragments thereof, or variants thereof to facilitate recovery of the fusion protein by affinity purification.

These include affinity tags, epitope tags and fluorescent tags such as the following.

Besides GST, affinity tags include a poly-histidine tag (His) typically comprising 6-8 histidine residues. The relatively small size of His tags makes its integration into expression vectors extremely easy. His-tagged proteins are purified using immobilized nickel, cobalt or zinc ions, and eluted using EDTA or imidazole. Since these tags do not form secondary structures to bind their substrate, you can easily purify your protein of interest even under denaturing conditions. During purification, ensure that EDTA and other metal chelators are avoided. EDTA is often present in commercial protease inhibitor cocktails. A Calmodulin Binding Protein (CBP) tag having a relatively small size of CBP (4 kDa) makes it ideal for purifying delicate proteins under mild conditions. The tag binds to a calmodulin resin and the proteins can be eluted with a neutral buffer containing low concentrations of EGTA, a calcium chelator. A maltose-binding protein (MBP): These tags bind to amylase agarose and are commonly used to increase the solubility of fusion proteins.

Epitope tags are typically smaller than affinity tags and are readily recognized by antibodies. Due to their relatively small size, they have extremely little or no effect on the structure of the resulting fusion protein. Epitope tags are ideal for several downstream applications which include western blotting, co-immunoprecipitation and immunofluorescence experiments. Some of the most popular epitope tags include the following: Myc tag—this tag is a short peptide sequence (EQKLISEEDL; SEQ ID NO: 3) derived from the c-myc gene product and recognized by numerous commercial antibodies. It can be added to a protein using recombinant DNA technology and may be used for affinity chromatography and for isolating protein complexes with multiple subunits. Human influenza hemagglutinin (HA) tag—the HA tag is a peptide sequence (YPYDVPDYA, SEQ ID NO: 4) derived from the surface glycoprotein that facilitates the ability of the influenza virus to infect its host and is recognized by numerous commercial antibodies. It is extensively used as a general epitope tag in expression vectors and is useful in facilitating the detection, isolation, and purification of your protein of interest. FLAG tag—like the Myc tag, the FLAG tag is a popular short peptide tag (DYKDDDDK, SEQ ID NO: 5) used in recombinant DNA technology and can be used for affinity chromatography and for isolating protein complexes with multiple subunits. It is recognized by numerous commercial antibodies, can be fused to the C-terminus or the N-terminus of a protein and can also be used with other affinity tags. The FLAG tag is more hydrophilic as compared to other tags in its class so they do not denature or inactivate the proteins to which they are attached.

Fluorescent Tags. Due to their non-toxic nature, these tags can be used to detect tagged proteins in both live and fixed cells. Green fluorescent protein (GFP) is one of the most widely used protein tags under this category. GFP is a protein isolated from the jellyfish *Aequorea victoria* that exhibits bright green fluorescence that does not fade easily when exposed to blue or ultraviolet (UV) light. By using GFP, one can determine whether a particular promoter was activated without going through the rigorous process of measuring mRNA levels. One can also use it to observe a particular protein as it performs its role within the cell. This particular tag is remarkably stable and can function when added to either end of a protein of interest.

Another embodiment of a method for making PDIA2 includes inducing expression of PDIA2 by contacting the host cells with isopropyl β-D-1-thiogalactopyranoside (IPTG) at a temperature of no more than 30° C. and/or by use of host cells contain extra copies of argU, ileY, and leuW tRNA genes.

In some embodiments, disrupting the cells induced to express PDIA2 is performed by contacting the induced host cells with lysozyme in the presence of at least one protease inhibitor and in the absence of glycylglycine or other solubility enhancers. In other embodiments, sonication, freeze-thawing, microfluidization, nitrogen or other gas decompression, physical cell disruption, shearing such as by French pressing may be used to disrupt the cells.

Following disruption, soluble and solid fractions of the disrupted cells may be prepared by centrifugation and/or filtration, e.g., filtration of a supernatant through a 0.45 or 0.22 micron filter. Soluble fractions of the disrupted cells may be applied to an affinity column that binds to GST or another tag on a fusion protein comprising PDIA2, a domain or active fragment of PDIA2 under conditions where the tag will bind to the fusion protein. The bound fusion protein may be washed and then eluted from the column.

A PDIA2 composition may be prepared in various forms, for example, as an oil-in-water or water-in-oil emulsion or the other formulations described herein.

For therapeutic use a composition containing PDIA2 typically is prepared aseptically and preferably in a sterile form along with excipient(s) that maintain the functional activities of PDIA2.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 1A. Overview of human PDI family members providing a list of 20 human PDI family members showing the name, length, ER localization and numbers of thioredoxin-like domains. Catalytic thioredoxin-like domains are shown in blue (a, a') with the active site sequence written in black and non-catalytic thioredoxin-like domains shown in pink (b, b'). The linker region (x) is shown in yellow. The transmembrane regions are colored green.

DETAILED DESCRIPTION OF THE INVENTION

Figure 1B:
FIG. 1B. Crystal structure of wild-type SOD1. Two identical polypeptide chains A and F, 153 amino acids in length are shown in green and blue respectively (PDB, 2C9V). Copper and zinc ions are present on each chain. Copper is represented as yellow spheres, zinc is represented as the larger red spheres.

In view of the many problems associated with expression of a soluble form of PDIA2, a eukaryotic protein, in a prokaryotic expression system the inventor has developed a method for obtaining soluble PDIA2 by expressing it in a prokaryote, such as *Escherichia coli* under particular conditions demonstrated to produce PDIA2 in a soluble form that can be further chromatographically purified.

The methods disclosed herein provides sufficient purified recombinant PDIA2 for use in cosmetics or therapeutic products that exploit the physiological properties of PDIA2 including the active or binding sites of the individual domains a, b, b', a'. Moreover, the PDIA2 containing compositions of the invention can contain additional active components such as superoxide dismutases like SOD1 and antioxidants which can supplement or complement the activity of PDIA2 in a cosmetic, therapeutic or other PDIA2 composition.

Expression of eukaryotic PDIA2 polypeptides in prokaryotic cells. Difficulties in expressing a eukaryotic PDIA2 polypeptide in a prokaryote cell in order to express PDIA2 in soluble form include codon bias or codon preference, protein folding, protein glycosylation, protein phosphorylation, and stability of eukaryotic mRNA in prokaryotes which express restriction enzymes that degrade foreign nucleic acids.

Some species use particular codons more frequently than others, exhibiting codon preference, or codon bias. Most amino acids are encoded by more than one codon and all the available amino acid codons are utilized as per the codon bias/preference of each organism. Transfer RNA (tRNA) of cells reflects the codon bias of its mRNA. Any heterologous gene with abundant codons, which are rarely used in bacteria, may not be properly expressed in bacteria, and may lead to translation errors. To attempt to avoid this problem, *Escherichia coli* cells such as BL21 Codon plus cells that contain extra copies of particular tRNA genes to compensate for differences between human and prokaryotic codon use are preferred in the present disclosure.

Expressed eukaryotic protein in bacterial cells are directed to three different locations: the cytoplasm, periplasm and in the growth medium through secretion. But often non-native disulphide formation occurs that leads to formation of insoluble aggregates and misfolding. As shown by the Examples, aggregation of PDIA2 with other proteins expressed by a prokaryote is a significant problem that prevents recovery of soluble PDIA2.

Bacteria have limited eukaryotic post-translational machinery function, which is considered as a significant disadvantage for producing the eukaryotic phosphoproteins i.e. serine/threonine/tyrosine protein kinases. Glycosylation is another major post-translational modification. It is responsible for the formation of cellular glycans which are often attached to proteins and lipids. Glycosyltransferase and glycosidases are enzymes responsible for glycosylation of many proteins. Glycoproteins, which are commonly distributed in eukaryotic cells, are rarely presented in prokaryotic organisms because cellular organelles essential for glycosylation are missing in these organisms. For example, N-linked glycosylation modulates dimerization of protein disulfide isomerase family A member 2 (PDIA2); Walker, et al., FEBS Journal 280:233-243 (2013)—incorporated herein by reference in its entirety.

Genes from different organisms tend to have different G+C content, with bacterial genes having a particularly low G+C content. A high A+T content in bacterial DNA often results in presence of sequences (AUUUA) that can destabilize mRNA. Moreover, prokaryotes often express restriction enzymes which efficiently degrade exogenous DNA or RNA such as nucleic acids encoding PDIA2.

Assays for PDIA2 functional activity, such as ELISA are known in the art and are commercially available.

The term "PDIA2" as used herein includes dimeric PDIA2, monomeric PDIA2, full-length PDIA2, a fragment of PDIA2 comprising a PDIA2 domain 1 (e.g., corresponding to residues 27-152 of SEQ ID NO: 2), or PDIA2 domain 2 (e.g., corresponding to residues 367-496 of SEQ ID NO: 2), or other fragments retaining at least one activity of full-length or dimeric PDIA2, such as chaperonin activity or ability to bind to estradiol or other estrogen or estrogen-like compounds.

This term also includes fusion proteins containing PDIA2 or an active fragment thereof. An example of a fusion protein is a GST-PDIA2 fusion protein construct.

In some embodiments, a fusion protein will contain a cleavage site between the amino acid residues of PDIA2 and exogenous residues, such as those of GST. In one embodiment, PDIA2 corresponds to Gene ID: 64714, last updated Feb. 13, 2019, incorporated by reference.

In another embodiment, the PDIA2 polypeptide is encoded by SEQ ID NO: 1 and its amino acid sequence is described by SEQ ID NO: 2. PDIA2 polypeptides as disclosed herein may contain 1, 2, 3, 4, 5, 6, 7, 8, 9, 10 or more amino acid residue deletions, substitutions or additions or have a sequence identity to the amino acid sequence of SEQ ID NO: 2 ranging from 80, 85, 90, 95, 96, 97, 98, 99, <100 or 100% to SEQ ID NO: 2. Variants of PDIA2 include natural variants or artificial variants comprising the following substitutions P39S, T119R, E185K, T286M, P382A, R388Q and P502S. Some variants will contain a mutation such as C18A which impairs disulfide bond formation, N284 which increases formation of stable disulfide bonded PDIA2 dimer, or C364A which has no effect on interchain disulfide bridge formation. Some variants will contain substitutions of one or more asparagine residues to modify glycosylation, for example, substitution of residues 127, 284 or 516.

The polynucleotide and polypeptide sequences disclosed herein for PDIA2 include those having sequence identity or similarity to the disclosed sequences, for example, that have between 70, 75, 80, 85, 90, 95, 96, 97, 98, 99, <100, or and 100% sequence identity or similarity to the disclosed polynucleotides or polypeptides. Typically, these variant proteins having substantial sequence identity or similarity will encode, or comprise, polypeptides that exhibit the same or similar properties as the disclosed sequence, for example, a variant PDIA2 protein will exhibit similar immunological, isomerase, chaperonin or estrogen sequestering properties to a PDIA2 encoded by SEQ ID NO: 1 or having the amino acid sequence of SEQ ID NO: 2. A PDIA2 or fusion protein containing PDIA2 may contain full-length PDIA2 or a fragment of PDIA2 such as a PDIA2 domain or fragment exhibiting PDIA2 enzymatic activity or an ability to bind to a PDIA2 substrates.

BLASTN may be used to identify a polynucleotide sequence having at least 70, 75, 80, 85, 90, 95, 96, 97, 98, 99, <100, or and 100% (or any intermediate %) sequence identity to a reference polynucleotide. A representative BLASTN setting optimized to find highly similar sequences uses an Expect Threshold of 10 and a Wordsize of 28, max matches in query range of 0, match/mismatch scores of 1/-2, and linear gap cost. Low complexity regions may be filtered/masked. Default settings are described by and incorporated by reference to hypertext transfer protocol ://blast.ncbi.nlm.nih.gov/Blast.cgi?PROGRAM=blastn&BLAST_PROGRAMS=megaBlast &PAGE TYPE=BlastSearch& SHOW_DEFAULTS=on&LINK_LOC=_blasthome (last accessed Apr. 8, 2019).

BLASTP can be used to identify an amino acid sequence having at least 70%, 75%, 80%, 85%, 87.5%, 90%, 92.5%, 95%, 96, 97.5%, 98%, 99%, <100% or 100% (or any intermediate %) sequence identity or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to hypertext transfer protocol ://blast.ncbi.nlm.nih.gov/Blast.cgi?PROGRAM=blastp&PAGE_TYPE=BlastSearch&LIN K_LOC=blasthome (last accessed Apr. 8, 2019).

The PDIA2 products discloses herein may be used in therapeutic products such as cosmetics, personal care products or skin care products. They may be incorporated into a composition applied topically to skin, mucous membranes or wounds or burns. While not being bound to any particular theory or mechanism of action, PDIA2-containing products can exert a positive effect on dermal or mucosal surfaces or promote healing by virtue of their chaperonin-like properties in folding new, or refolding damaged, proteins, for example, through forming disulfide bonds via its thiol isomerase, oxidase and reductase activities as well as their ability to sequester estrogens. In one embodiment, a PDIA2 composition of the invention may be applied to mucosal tissue, buccal or oral tissue, or gastrointestinal tissue, for example, to promote healing of burns or other lesions. In another embodiment, a PDIA2 composition as disclosed herein may be administered to pancreatic tissue or other tissue that naturally expresses PDIA2.

In a preferred embodiment of the invention the PDIA2-containing composition is used to treat damaged mucosal tissue in an area of high vascular activity such as an inner eyelid tissue. Surgical procedures such as blepharoplasty or other surgical techniques used to remove adipose and/or other tissues from underneath the eyelids may lead to damaged mucosal tissues, especially at a subcutaneous tissue area in proximity to the orbicularis oculi or conjunctiva. The highly vascular characteristics of the conjunctiva on the inside of eyelids lends itself well to treatment with PDIA2-containing composition. Importantly, however, the PDIA2-containing composition must be held fast to the conjunctiva for a prolonged period (from several hours to several days) in order to maintain physical support for the damaged tissue and to permit longer-term contact of PDIA2 material with the damaged tissue. Preferably the PDIA2 is contacted with the inner surface of an eyelid and/or conjunctiva tissues with a gel insert that may be held in place on an inner surface of an eyelid through one or more adhesives holding a contact point inside the eyelid or extending away from the conjunctiva to an outer portion of the eyelid for connection with a relatively drier portion of eyelid skin or epidermis. The gel insert is preferably a gelatin-based or hyaluronic acid-based material in the form of a pad or oblong shape that typically extends along a portion of the damaged conjunctiva. The gel pad is preferably constructed such that PDIA2 protein or PDIA2-containing composition is present on only the one surface of the pad which is in direct contact with the conjunctiva. The pad is therefore a support mechanism having a surface onto which the PDIA2 or PDIA2-containing composition is coated. This coated surfaces being directly contacted with the conjunctiva for a period of time sufficient to improve the condition of damaged tissue which is in contact with the PDIA2-coated gel pad. Treatment times are typically hours to days with the preferred treatment time of about 6 hours upon which the gel pad and PDIA2 are replaced with a new pad upon examination.

PDIA2 also can modulate the level or activity of estrogens such as estradiol via its ability to bind to these compounds. By binding to PDIA2 environmental endocrine disruptors which exert estrogen-like activities can be sequestered. Compositions containing PDIA2 can be formulated to reduce the level of estrogens and endocrine disruptors that bind to PDIA1, for example, in personal care and cosmetic products for men's or women's skin or for subjects exposed to exogenous estrogens.

Therapeutic Compositions of the Invention. Compositions useful herein include any composition that is able to carry or incorporate PDIA2 in an active form, such as a form which can prevent misfolding of proteins, correct protein misfolding, modulate estrogen activity, bind to or sequester estrogens, bind to or sequester environmental endocrine disrupters; reduce the growth or proliferation of cancer cells, or induce cytotoxicity against cancer cells.

Typically, a PDIA2 composition if formulated for application to skin or a mucous membrane, such as to skin exposed to harsh conditions that denature proteins including heat, dryness, cold, chemicals, UV, viral, bacterial, fungal or other microbial infection, or to tissue damaged by inflammation, allergy or autoimmunity. It may be applied to a mucous membrane such as those in the eyes, nose, mouth, GI tract, respiratory system, or genitals.

In some embodiments, a PDIA2 composition may be formulated for application into or on a wound or lesion to prevent denaturation of proteins in internal tissues exposed to air, antiseptics, microorganisms, or other denaturing conditions, for example, a composition may be incorporated into glue or adhesive, salve, or ointment for application to a wound or into a suture, band aid, or gel for application to a wound. In some embodiments a PDIA2 composition may be administered internally, such as intradermally, intramuscularly, intravenously, or by other parenteral routes. Such compositions are generally formulated to allow for administration to a subject by any chosen route and usually contain one or more further excipients, such as a stabilizer or preservative for the PDIA2, buffer, diluent or other excipient based on an intended route of administration. For example, when formulated for administration to the skin, hair or nails the composition will contain excipients suitable for topical administration and when administered onto a mucous membrane it will contain suitable excipients. For example, a PDIA2 composition may be formulated as an eye drop, lubricating or tear replacing solution containing a saline solution and hydroxypropyl methylcellulose (ophthalmic) or carboxymethylcellulose. Depending on the condition being treated, it may contain, in addition to PDIA2, steroids, antihistamines, sympathomimetics, beta receptor blockers, parasympathomimetics, parasympatholytics, prostaglandins, nonsteroidal anti-inflammatory drugs (NSAIDs), antibiotics, antifungal, or topical anesthetics. Conventional eye drops, which do not have medications in them and are only lubricating and tear-replacing solutions, may be supplemented with PDIA2. In other embodiments, a PDIA2 composition may be formulated with physiological saline or other suitable excipient as a nasal rinse to treat sinus conditions or as a topical spray or emollient to wash or rinse wounds, including post-surgical wounds, stitches, scabs, or other skin conditions.

The preparation of pharmaceutically acceptable carriers and formulations suitable for containing PDIA2 is described in *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety.

A composition may have an acidic or basic pH, such as a pH ranging from 1, 2, 3, 4, 5, 6, 7, 8, 9, 10, 11, 12, 13 to 14 (or any intermediate value within this range), preferably from 3 to 9, more preferably from 5.5 to 8.5. It may match or coordinate to the pH of the skin (e.g., from pH 4 to 7.0, preferably about pH 5), nails or hair, or other tissue to which it is applied or vary upward or downward by about 0.1, 0.2, 0.3, 0.4, 0.5, 0.6, 0.7, 0.9, 1.0, 1.5 or 2.0 pH units from a neutral pH or from the pH of skin, hair, nails, mucosal, or other tissue to which it is applied.

Compositions, including topical compositions, may be prepared as solutions, serums, lotions, creams, pastes, ointment/salves, gels, aerosols, foams and other conventional formulations using known carriers for such applications. Such formulations may be administered directly, for example, applied directly to a dermal site such as the site of a burn, abrasion, acne, infection, or a wound. It may be applied by hand or mechanically, such as by spraying or by impregnation into a bandage, dressing, or adhesive or non-adhesive gel or other covering.

A composition containing PDIA2 may contain stabilizers, preservatives, humectants, regreasing agents, solvents or auxiliaries to improve efficacy and penetration into the dermis or other tissue. Penetration-enhancing compounds include propylene glycol, polyethylene glycol, dimethyl sulphoxide, decylmethylsulphoxide, azoles, N-methylpyrrolidone, diethyltoluamide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants.

Viscosity enhancers or thickeners can be included, for example to prevent a composition from spreading beyond the site of application. Thickeners include carbomer, hydroxypropyl methylcellulose, hydroxyethylcellulose, PVM/MA decadiene cross-polymer and acrylates.

In some embodiments, a PDIA2 composition may contain hyaluronic acid, collagen, elastin, or other components of the skin. Hyaluronic acid is a substance that is naturally present in the human body and may be extracted from rooster combs or made by recombinantly. Hyaluronic acid is also used as a lip filler in plastic surgery and may be applied to the skin for healing wounds, burns, skin ulcers, and as a moisturizer.

In other embodiments, a PDIA2 composition may contain an antioxidant such as Vitamin A, C or E, cysteine, thiols, thyoredoxins, glutathione, or enzymes like catalase or superoxide dismutase. Vitamins D or K may be included as well as the B vitamins. For example, an antioxidant may be incorporated to reduce the number of disulfide bonds in a denatured protein and facilitate is refolding by PDIA2.

Superoxide dismutases catalyze the dismutation of the superoxide ($O_2^-$) radical into ordinary molecular oxygen ($O_2$) or hydrogen peroxide ($H_2O_2$). Superoxide is produced as a by-product of oxygen metabolism and, if not regulated, causes many types of cell damage. Hydrogen peroxide is also damaging and is degraded by other enzymes such as catalase. SOD is an important antioxidant defense in nearly all living cells exposed to oxygen. SODs include Cu/Zn type (which binds both copper and zinc, such as SOD1), Fe and Mn types (which bind either iron or manganese), and the Ni type (which binds nickel). In some embodiments human or mammalian SODs such as Cu/Zn type SOD1 are used in a PDIA2 composition. In other embodiments prokaryotic SODs may be used. One or more SODs may be used in combination with PDIA2 or other active ingredients in a PDIA2 composition of the invention. By way of general example, from about <1, 1, 2, 5, 10, 20, 50, 100, 200, 500, 1,000 µg or 1, 2, 5, 10, 50, 100 or >100 mg per kg body weight may be administered.

Spreading oils or emollients can be included in the PDIA2 composition. One benefit for including such oils is for better distribution on surfaces, in particular on the skin. Spreading oils are understood as those oily liquids which are distributed particularly easily on the skin. Suitable spreading agents can include silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parabens, pH adjusting agents, surfactants, chelators, such as disodium EDTA or sodium citrate, tackifying agents, fragrances and other compounds.

Any effective concentration of PDIA2 may be incorporated into a composition. These include, but are not limited to >0, 0.001, 0.002, 0.005, 0.01, 0.02, 0.05, 0.1, 0.2, 0.5, 1.0, 2.0, 5.0, 10.0, 20.0, 50.0 and <100 wt % of PDIA2. These ranges include all intermediate values and subranges.

A serum refers to a light, quickly absorbed composition that exposes and permits rapid uptake of an active ingredient by skin. It can be used as an alternative to heavier creams or lotions that contain occlusive, or airtight, moisturizing ingredients such as petrolatum or mineral oil that keep water from evaporating. Serums usually contain fewer lubricating and thickening agents, like nut or seed oils, than creams or lotions. Most serums are water-based or based on hydrophilic components, eliminating oils altogether. A serum may be formulated to contain a higher concentration of PDIA2, than a cream or lotion.

Lotions described herein include liquids or semi-liquid formulations that are generally lower in viscosity than a cream or gel. The lotions can be an oil-in-water or water-in-oil formulation stabilized by a surface-active agent and are usually suitable for application to skin, hair or nails. They may be in a form of an emulsion and include methylcellulose, sodium carboxymethyl-cellulose, and similar compounds or contain other ingredients such as those described below for creams and other pharmaceutical compositions provided the combined amounts of the ingredients form a lotion. In one embodiment, the lotions contain suspending agents to produce better dispersions and compounds useful for localizing and holding PDIA2 once applied.

Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. The oil phase can comprise petroleum jelly and a fatty alcohol, such as cetyl or stearyl alcohol. The aqueous phase can contain a humectant. The emulsifier can be a nonionic, anionic, cationic or amphoteric surfactant. In one embodiment, the oil phase includes, but is not limited to, cetyl alcohol, stearyl alcohol, stearic acid, liquid paraffin, and dimethicone.

Ointments/salves incorporating PDIA2 include semi-solid preparations that have petroleum jelly or their derivatives as a base. Petroleum jelly is a semi-solid mixture of hydrocarbons. As described in *Remington: The Science and Practice of Pharmacy,* 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid. An ointment may contain solid or encapsulated particles or emulsified and suspended particles of PDIA2. Black Ointment, or Ichthyol Salve, also called Drawing Salve may be modified to contain PDIA2. Drawing salve has been traditionally used to treat minor skin problems such as sebaceous cysts, boils, ingrown toenails and splinters. The main ingredients are often ichthammol, phenyl alcohol, or *Amica montana*, and may contain herbs such as *Echinacea* or calendula.

Pastes incorporating PDIA12 can contain, in addition to an ointment or cream base, high amounts of pulverulent constituents, such as zinc oxide, talc, starch or titanium dioxide. In one embodiment, the paste is selected from the group comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds. A paste may contain solid or encapsulated particles or emulsified and suspended particles of PDIA2. One example of a paste is a sunscreen containing PDIA2 in a biologically available form for inhibiting denaturation of skin proteins by UV exposure.

Gels provided herein include semi-solid suspensions that contain PDIA2. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic. In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinyl alcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In another embodiment, the organic macromolecules having a stabilizing action include long-chain linear high molecular weight polysaccharides with a molecular weight of more than one million. In another embodiment, a uniform gel can be prepared by adding dispersing agents such as alcohol or glycerin. In another embodiment, the organic macromolecules can be dispersed by trituration, mechanical mixing or stirring, or combinations thereof. In another embodiment, the liquid can be either water or all water-miscible solvents. Examples of applicable solvents include alkanols, such as ethanol and isopropyl alcohol, benzyl alcohol, propylene glycol and similar solvents.

Hydrogels containing cross-linked insoluble starch or carboxymethylcellulose polymers and water and PDIA2 may be applied to skin, a burn or a wound or other tissues in need of PDIA2.

Hydrocolloid dressings containing polymers such as gelatin, pectin and cellulose and PDIA2 and which form a waterproof adhesive dressing may be used to treat a skin disorder, burn or wound or other tissue in need of PDIA2.

Alginate dressings containing PDIA2 may also be used for skin disorders, burns or wounds or other tissues in need of PDIA2. These tend to be highly absorbent and are available in two forms; calcium alginate and calcium sodium alginate. The use of alginate dressings as hemostatic agents was reported both in vitro and in clinical studies. The selection of an alginate dressing is usually to manage wound exudate, as it is claimed that they can absorb 15-20 times their own weight in wound fluid. The alginate forms a gel when it comes into contact with the wound surface. It can be used in granulating, epithelializing, and cavity wounds.

Aerosols as provided herein include PDIA2-containing products packaged under pressure and contain ingredients that are released upon activation of an appropriate valve system. Aerosols include all self-contained pressurized products, such as fine mists of spray or foam, that are emitted from a pressurized container containing a propellant, foams, or semisolid liquids. They may also be emitted by an unpressurized atomizer that is pressurized by a hand-operated pump rather than by stored propellant. In one embodiment, the aerosol comprises a container, a propellant, a concentrate containing an active ingredient, a valve (which may be a metered valve), and an actuator. The nature of these components determines characteristics such as delivery rate, foam density, and fluid viscosity. In another embodiment, the aerosol is a two-phase formulation comprising a gas and liquid. In another embodiment, the aerosol is a three-phase formulation comprising a gas, liquid, and suspension or emulsion of active ingredients. In this formulation, suitable excipients, such as wetting agents and/or solid carriers such as talc or colloidal silicas are included. In another embodiment, the propellant is liquefied or vaporized. In another embodiment, a solvent can be the propellant or a mixture of the propellant and co-solvents such as alcohol and polyethylene glycols. In another embodiment, the propellant is selected from the group comprising a spray, foam, or quick-breaking foam. In another embodiment, spray formulations are aqueous solutions in a container having a spray means, such as an atomizer or nebulizer. An aerosol may contain solid or encapsulated particles, emulsified and suspended particles, or liquid or atomized droplets containing PDIA2.

Foams. In some embodiments, PDIA2 is delivered to the body while in a foam state, such as stable foam, for example, that is produced with or without a propellant. For example, the extract may be contained in a shaving foam and used for preventing bacterial infection of nicks, cuts or abrasions associated with shaving. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam. Active ingredients in a foam may be dispensed for subsequent placement on a dry wipe, a pre-moistened wipe, or other soft, flexible applicator (e.g., an object about 3-fingers wide or 4 to 10 cm wide) or other object to be used for application of the foam-based composition to the skin. The foam can be a non-propellant foam. A foam with a suitable stiffness of yield stress can be applied to the skin in any manner for sustained adherence and contact with the body. Examples of foam-based systems are described in U.S. Pat. No. 6,818,204, "Stable Foam for Use in Disposable Wipe," herein incorporated by reference. That patent involves the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™, anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, a surfactant is present in an amount from about 2% to about 35% by weight, or from about 5% to about 15% by weight (or any intermediate value or subrange).

At least one foam stabilizing agent may be present in some foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%. In U.S. Pat. No. 6,818,204, alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%. The ranges above include all intermediate values and subranges.

A foam may be produced using the F2 Finger Pump Foamer™. manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein. Details of exemplary propellantless defoamers are described in U.S. Pat. Nos. 5,443,569 and 5,813,576 herein incorporated by reference.

Encapsulation. PDIA2 as described herein can be encapsulated in a carrier such as in liposomes, micelles, or microspheres. Suitable carriers are described in U.S. Pat. No. 7,205,003, hereby incorporated by reference. Encapsulation of PDIA2 may be used to prevent its digestion in the stomach and permit its passage through stomach acid into the intestines.

Micelles provided herein can comprise surfactant molecules arranged such that their polar head groups form an outer spherical shell, while their hydrophobic, hydrocarbon chains are oriented towards the center of the sphere, forming a core. The precursor and PDIA2 are encapsulated within the core of the micelle. Surfactants suitable for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Liposomes provided herein are microscopic vesicles having a lipid wall comprising a lipid bilayer. Liposomal preparations herein include cationic (positively charged), anionic (negatively charged), and neutral preparations including PDIA2. Cationic liposomes include N[1-2,3-dioleyloxy)propyl]-N,N,N-triethylammonium (DOTMA). Anionic and neutral liposomes can be easily prepared using materials such as phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE). These materials can also be mixed with DOTMA in appropriate ratios.

Microspheres provided herein can comprise micro- or nano-scale carriers that are made of polymers, both synthetic and natural and which contain PDIA2. Additional nomenclature describing microspheres include, but are not limited to, spheres, beads, particles, carriers, microbeads, microparticles, microcarriers, nanospheres, nanobeads, nanoparticles, and nanocarriers.

Polymeric materials suitable for the microspheres provided herein include those that are described in U.S. Pat. No. 6,423,345, hereby incorporated by reference in its entirety for all purposes, including poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Natural polymers including agarose and alginate are also suitable for the microspheres. Any of the above carriers can include proteins, lectins, and other biological materials. The precursors and activating agents can be encapsulated into the carriers using known techniques in the art, including microspheres described in U.S. Pat. No. 6,423,345, incorporated by reference, including solvent evaporation, hot melt microencapsulation, solvent removal, and spray drying of microspheres. In one embodiment, the microsphere comprises a block copolymer. In another embodiment, the microsphere comprises a hydrogel.

Sustained-release formulations may be prepared. Suitable examples of sustained-release preparations include semipermeable matrices of solid hydrophobic polymers containing the desired antifungal agents. The matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides (see U.S. Pat. No. 3,773,919, incorporated by reference), copolymers of L-glutamic acid and ethyl-L-glutamate, non-degradable ethylene-vinyl acetate, and degradable lactic acid-glycolic acid copolymers such as the LUPRON DEPOT™ (injectable microspheres composed of lactic acid-glycolic acid copolymer and leuprolide acetate). Compositions useful herein may be adapted for immediate, delayed, modified, sustained, pulsed or controlled release of a compound of the invention. For example, a wound dressing or composition applied to the skin, hair or nails may be formulated to release the active compounds over a period of 1-24 hours or 1-14 days (e.g., where skin or a treatment site is substantially immobilized (patients immobilized in a bed or covered by a cast, bandage, etc.) or any intermediate period of time.

Suppositories. In addition to the active PDIA2 component, a suppository may contain the customary water-soluble or water-insoluble excipients, for example polyethylene glycols, fats, for example cocoa fat and high glycerol monostearate; adsorption agents, for example kaolin and bentonite; and lubricants, for example talcum, calcium stearate and magnesium stearate, and solid polyethylene glycols or mixtures of the substances mentioned above. In some embodiments, the active ingredient(s) can be in a microencapsulated form in the tablet or capsule, which can optionally be formulated to esters (e.g., $C_{14}$-alcohol with $C_{16}$-fatty acid) or mixtures of these substances.

Tablets, Capsules, Pills. In some embodiments, PDIA2 can be formulated as a tablet, capsule or pill. These may contain the customary excipients, such as fillers and extenders, for example starches, lactose, sucrose, glucose, mannitol, and silicic acid; binders, for example carboxymethyl cellulose, alginates, gelatin, polyvinylpyrrolidone; humectants, for example glycerin; disintegrating agents, for example agar-agar, calcium carbonate and sodium carbonate; dissolution retardants, for example paraffin; resorption accelerating agents, for example quaternary ammonium compounds; wetting agents, for example cetyl alcoholrelease the active PDIA2 component at a particular location within the GI tract, e.g, to transit the stomach and release the active component in the small or large intestine.

Capsules can contain PDIA2 and any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tableting agent.

Powders may be formulated to contain dry or encapsulated PDIA2 and the customary excipients, for example lactose, talcum, silicic acid, aluminum hydroxide, calcium silicate, and polyamide powder, or mixtures of these substances. Such powders may be formulated for topical application or for inhalation.

Personal Care Products may be formulated to contain PDIA2. These may be used as preventative care products to prevent ring worm and other skin infections or as deodorants or personal care products that prevent the formation of body odors or rough skin. The PDIA2 may be incorporated into conventional body washes, lotions, lubricants, personal care compositions, exfoliants, shaving creams, aftershaves, colognes, beard oils, antiperspirants, or deodorants. Such products are well known in the art and commercially available and are also described by Broad, U.S. Pat. No. 4,252,789, which is incorporated by reference, especially for their descriptions of conventional deodorant ingredients, formulations, and modes of use. These products can be applied to the axilla, inguinal region, feet or other odor-producing, moist or intertriginous or interdigital body part to prevent growth of odor-causing microorganisms. In other embodiments, the extract of the invention can be incorporated into a deodorizer, cleaner, or disinfectant such as a liquid sanitizer or disinfectant, a spray or wipe for cleaning surfaces exposed to bacterial contaminants.

Other personal care products include cosmetic compositions such as nail care compositions such as nail (finger and toe) polish and nail polish removers, and makeup products that contain a color deposited onto a keratinous substrate such as skin, lips, and lashes. Makeup products include primers, lipstick, lip gloss, lip plumper, lip liners, lip balms, eyeliners, eyeshadows, masara, concealers, rouges, foundations, face powders, highlighters, contour powders or creams, bronzers, eyebrow definers, and setting sprays for makeup. A cosmetic composition can be in many different forms, including liquid or cream emulsions; powders that are pressed, cast, or loose; dispersions, and anhydrous creams or sticks; or solids such as pencils and the aforementioned powders and sticks; shower and bath compositions containing the lipophilic hydroxytyrosol carbonate ester compounds include but are not limited to body washes (including moisturizing body wash), shower gels, skin cleansers, cleansing milks, in shower body moisturizer, and pet shampoo; hair care compositions include shampoos, hair conditioners, colorants, dyes, bleaches, straighteners, and permanent wave products; infant care compositions include infant shampoo, infant body wash, and infant bubble bath; skin care compositions include shaving compositions, cleansing compositions, emollients, moisturizing compositions including anti-aging compositions; exfoliant compositions, face masks, and skin toners, and compositions containing pharmaceutically active ingredients for reduction of skin irritations, rashes, inflammations, and eczema; and sun care compositions including compositions containing UV blocking agents (UVA and/or UVB), such as sun tan compositions, sunscreen compositions having an SPF rating of 20 or more, or 30 or more, or 40 or more, or 50 or more; and lip balms and lip care for protection against wind and sun. Sun care compositions may also include sunless tanning treatments.

A personal care composition may be in any of the forms described above including in the form of lotions, oils, creams, gels, and sprays. A personal care composition may contain carriers, cleansing agents, emollients, moisturizers or hydrating agents, active anti-aging or anti-wrinkle agents, pigments, colorants, fragrances, biocides, preservatives, antioxidants, antiperspirant agents, exfoliants, hormones, enzymes, medicinal compounds, vitamins, ultraviolet light absorbers, skin bleaching agents, anti-acne agents, botanical extracts, silicone oils, organic oils, waxes, adhesion promoters, plasticizers, film formers, including hair fixatives, thickening agents, fillers and binders, alcohol and other organic solvents, and propellants.

Parenteral formulations and dosage forms include aqueous solutions, isotonic saline or glucose solutions comprising the active agent, or other well-known pharmaceutically acceptable carriers. Solubilizing agents well-known to those familiar with the art can be used as pharmaceutical excipients. Injectable dosage forms may be formulated as liquid solutions or suspensions. Solid forms suitable for solution in, or suspension in, liquid prior to injection may also be prepared.

It should be understood that the PDIA2 and other additional agents listed above may also be employed in a method of the invention where they are administered separately, simultaneously or sequentially with a compound, isolate or composition useful herein.

As will be appreciated, the dose of the composition administered, the period of administration, and the general administration regime may differ between subjects depending on such variables as the severity of symptoms of a subject, the type of disorder to be treated, the mode of administration chosen, and the age, sex and/or general health of a subject. However, by way of general example, from about <1, 1, 2, 5, 10, 20, 50, 100, 200, 500, 1,000 μg or 1, 2, 5, 10, 50, 100, to >100 mg per kg body weight may be administered. Administration may include a single dose, such as a single daily dose, or administration of a number of discrete divided doses as may be appropriate. A person of ordinary skill in the art will be able to determine without undue experimentation, having regard to that skill and this disclosure, an effective dosage regime (including dose and timing of administration) for a given condition.

When used in combination with an additional agent, the administration of a compound useful herein and the other agent may be separate, simultaneous or sequential. Simultaneous administration includes the administration of a single dosage form that comprises all components or the administration of separate dosage forms at substantially the same time. Separate or sequential administration includes administration according to different schedules, preferably so that there is an overlap in the periods during which the composition useful herein and other therapeutic agent are provided.

Additionally, it is contemplated that a composition in accordance with the invention may be formulated with additional active ingredients such as other forms of PDI, SOD, or antioxidants.

PDIA2 as well as other active ingredients such as other PDIs or SOD may be incorporated into a skin protectant or skin restoring product, such as an ultraviolet protectant, sunscreen, sunblock or post-UV exposure protectant. These products typically contain one or more occlusive agents which create a barrier that blocks water from escaping the skin, such as petrolatum, mineral oil and/or dimethicone; one or more humectants, which are ingredients that attract water, such as glycerin or glycerates; and one or more emollients, such as coconut oil, cetyl esters, and silicones; which improve the feel of a protectant on the skin and reduce the tackiness and greasiness caused by the other moisturizing ingredients. In some embodiments at least one compound that screens out, filters, or blocks UV radiation may also be incorporated. Such compounds include para-aminobenzoic acid (PABA), padimate O, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium oxide, zinc oxide and mixtures thereof. Compared to conventional sunscreens or sunblocks, the composition of the invention contains PDIA2 which further protects against misfolding of, or repairs, skin proteins by exposure to harsh conditions, such as to directly sunlight on a beach.

Application of the protectant prevents or and ameliorates misfolding of skin proteins caused by exposure of the skin to the environment, such as excessive exposure to UV radiation, salt water, dryness and heat, or freezing conditions, associated with the development of wrinkles and sagging skin providing advantages that a sunscreen containing only a UV blocker but not PDIA2 or SOD1 cannot.

As shown by the examples below, the inventor has developed a way to produce and isolate PDIA2 by expressing it in prokaryotic cells.

EXAMPLES

Preparation of competent cells. The appropriate *E. coli* strains, BL21 codon plus and XL-1 blue inoculated in LB broth for overnight at 37° C.

A sufficient amount of overnight culture was added to fresh 100 ml LB such that the starting optical density at 600 nm ($OD_{600}$) reached 0.1. The culture was incubated at 37° C. until the $OD_{600}$ reached between 0.5-0.6 (cells growth phase). The cells were centrifuged at 600 g for 15 min at 4° C. and the pellet resuspended in 100 mM cold $CaCl_2$. The solution was incubated on ice for 15 min and then centrifuged again at 600 g for 10 min at 4° C. The pellet was resuspended in 85 mM $CaCl_2$ with 15% (v/v) glycerol, snap frozen in liquid nitrogen and stored at −80° C.

Transformation. Competent cells were thawed on ice. Plasmid DNA (50 ng) was mixed with 50 µl of competent cells. The mixture was incubated on ice for 15 min followed by a heat shock for 30 second at 42° C. and back on to ice again for 1 min. Fresh LB medium (100 µl) was add and incubated at 37° C. for 1 hour. The transformation mixture was plated on the LB agar plate with (100 µg/ml) ampicillin. The plates were incubated overnight at 37° C.

Isolation of Plasmid DNA. A colony transformed with the desired plasmid was inoculated into 2 ml of LB medium with ampicillin (100 µg/ml), and incubated overnight at 37° C. The culture was centrifuged at 2500 g for 5 min. The supernatant was discarded and the pellet was resuspended in 100 µl of cold homogenization buffer (50 mM glucose, 10 mM EDTA and 25 mM Tris-Cl pH 8.0). The resuspension was allowed to incubate for 5 min at room temperature. Freshly prepared lysis buffer (200 mM NaOH and 1% SDS) was added in order to lyse the cells. Samples were incubated for 5 min at room temperature. Neutralisation buffer (3 M potassium acetate, pH 5.0) was added and samples were gently mixed and incubated on ice for 5 min, followed by the addition of 2 M LiCl. The samples were centrifuged at 18000 g for 5 min. Clear supernatant containing the plasmid DNA was transferred to a new tube and 500 µl of cold isopropanol was added. The contents were centrifuged at 18000 g for 5 min to pellet the plasmid DNA. The pellet was washed with 70% ethanol and air dried. The pellet was resuspended in 30 µl Milli-Q $H_2O$ with RNase (10 mg/ml). To achieve high yield plasmid DNA isolation, a midi prep isolation kit (Qiagen) was used according to the manufacturer's protocol.

Agarose Gel Electrophoresis. The percentage of agarose gel depends on the size of the DNA fragment being analysed (Harwood, 1996). Agarose gels 1% (w/v) were prepared in TAE buffer (40 mM Tris, 0.0114% (v/v), 1 mM EDTA) with 0.4 µg/ml of ethidium bromide. Loading dye (0.04% (w/v) xylene cyanol, 0.04% (w/v) bromophenol and 5% (v/v) glycerol) was added to DNA samples prior to electrophoresis. Determination of the size of DNA fragments was obtained by using 1 kb plus DNA ladder (Invitrogen). Gels were electrophoresed at 110 V for 45 minutes. A Gel doc-it™ imaging system (UVP) was used to visualize the gel.

DNA Sequencing. DNA samples (500-1500) ng were mixed with 10 pmol of appropriate forward primer, and reverse primer respectively. The final volume was adjusted to 12 µl with sterile water.

Protein Expression. A single colony was inoculated into 2 ml of LB media with ampicillin (100 µg/ml) and grown at 37° C. for overnight. The culture was transferred into 10 ml fresh LB media containing ampicillin (100 µg/ml) such that the initial OD600 was 0.1. The growth was monitored until the desired $OD_{600}$ was achieved (0.5-0.8). A pre-induction sample (−IPTG) was taken as a negative control, centrifuged at 1100 g for 5 min and the pellet was stored at −20° C. To the remaining culture 0.1 mM of IPTG was added and incubated for 4 hours at 37° C. A sample of culture was collected and the $OD_{600}$ value was recorded. The sample was harvested by centrifugation at 1100 g for 5 min, and pellet stored at −20° C. The pellet was resuspended in phosphate buffered saline (PBS) (0.137 M NaCl, 2.7 mM KCl, 0.01 M $Na_2HPO_4.2H_2O$, 2 mM $KH_2PO_4$) with SDS loading dye (4 mM Tris-Cl pH 6.8, 0.4% (w/v) SDS, 20 mM DTT, 2% (v/v) glycerol, 0.02% (w/v) bromophenol blue). For high yield of protein, large scale expression was performed in a similar method to the small scale expression that described above except that 500 ml and 4000 ml LB was used instead of 10 ml LB, and the culture was incubated overnight at 16° C. with 0.1 mM IPTG. Following overnight incubation, the culture was centrifuged at 2500 g for 20 min at 4° C. The cell pellets were stored at −20° C. for cell lysis. Protein samples were analysed using SDS-PAGE gels.

Cell Lysis. The pellets from large scale expression were resuspended in PBS containing complete EDTA-free protease inhibitors (Roche) and lysozyme enzyme (1 mg/ml). The suspension was incubated for 15 min at room temperature. The mixture was subjected to rapid freeze-thaw 3 times by snap freezing the cells in liquid nitrogen and thawing them in a water bath at 37° C. DNase (10 µg/ml) was added to the samples, and the mixture was incubated at room temperature for 15 min. The cell lysate was centrifuged at 12,000 g for 30 min at 4° C. The supernatant and pellet were separated in different tubes. Solubility of the proteins was analyzed using 12% (w/v) Tris glycine SDS-PAGE gels.

SDS-PAGE. Tris-glycine SDS gels were composed of a 12% separating gel and a 5% stacking gel. The major differences between those gels the pH and acrylamide concentration to obtain beneficial separating and sharper bands in the separating gel. Separating gel was made using 12% acrylamide, 4 M Tris-HCl pH 8.8, 0.1% (w/v) SDS, 0.1% (w/v) ammonium persulfate (APS) and 0.08% N,N,N',N'-tetramethylethylenediamine (TEMED) whereas the stacking gel was composed of 5% acrylamide, 1M Tris-HCl pH 6.8, 0.1% (w/v) SDS, 0.1% (w/v) APS and 0.2% TEMED. The samples were mixed with SDS loading dye and denatured at 95° C. for 5 min. Protein samples (20 µl) were run alongside 5 µl of a protein ladder See Blue plus 2 pre-stained standard (Invitrogen). Electrophoresis was carried out at 25 mA for approximately 1 hour in the presence of SDS running buffer (25 mM Tris, 0.1% (w/v) SDS, 250 mM glycine pH 8.30). Coomassie blue stain (40% (v/v) methanol, 0.1% Coomassie Brilliant Blue R250 (Sigma), 10% acetic acid) was used to stain gels overnight. Destaining was performed by using destain solution (40% methanol, 10% acetic acid) for overnight.

Protein Purification-GST Matrix Equilibrium. Glutathione sepharose beads (GE healthcare) (200 µl) were washed 4 times with 4 ml PBS for the efficient removal of the residual ethanol and centrifuged at 600 g for 5 min. The supernatant was decanted and a 50% slurry was prepared by resuspending the beads in an equal amount of PBS.

Protein Purification-Purification of Soluble Proteins. Supernatant samples from cell lysis were transferred to the equilibrated beads and incubated at 4° C. on a rotating mixer for 2 hours. The samples were centrifuged at 700 g for 5 min and the supernatant was collected as an unbound sample. The beads were washed with PBS buffer and centrifuged at 700 g for 5 min. The supernatant was kept as the wash (1) fraction. This step was repeated 4 times, and the supernatant was collected each time. The beads were incubated in elution buffer (20 mM glutathione in 50 mM Tris-HCl pH 8.0) for 5 min on ice and centrifuged at 700 g for 1 min. The elution step was performed 5 times and all supernatants were kept as different elution fraction. The samples were subjected to SDS-PAGE for analysis.

Western Blotting. The SDS-PAGE gel was transferred onto a nitrocellulose filter (NCF) for 1 hr and 15 min at 90 mA by using semi-dry transfer in a western transfer buffer (25 mM Tris-Cl, 192 mM glycine, 0.03% (w/v) SDS, 20% (v/v) methanol). To observe the efficiency of the transfer, the NCF membrane was stained with Ponceau S stain (1% (v/v) glacial acetic acid, 0.5% (w/v) Ponceau S) for 5 min and then destained with sterile water for the same period. The membrane was blocked by incubating in blocking agent (5% (w/v) skim milk in 50 ml of 0.1% (v/v) PBS-Tween (PBST) overnight at 4° C. The NCF membrane was washed 4 times with PBST for 5 min each time. It was incubated with the primary antibody (anti-GST mouse) for 1 hr. The membrane was washed 4 times with PBST and incubated with secondary antibody (HRP-conjugated rabbit anti-mouse IgG (1:50, 000) in PBST for 1 hr at room temperature. A final wash of the NCF with PBST was carried out and protein bands were detected by added chemiluminescent agent (ECL) (GE healthcare) to the membrane. Bands were visualised either by using a chemi doc™ XRS (BIO-RAD) or hyperfilm cassette (GE healthcare).

Mass Spectrometry. The coomassie stained protein band was cut out from the SDS-PAGE gel carefully then transferred into 10 mM Tris-HCl (pH 8.0-9.0) and incubated overnight. Dithiothreitol (DTT) (10 Mm) was added and incubated for 1 hr at 60° C. to denature any disulphide bonds. Indole-3-acetic acid (IAA) 50 mM was added and the sample was incubated in the dark for 30 min at room temperature. Removing the stain from the gel was performed by the addition of 400 µl of 50% acetonitrile (ACN) in 25 mM ammonium bicarbonate (ABC) and shaking for 20 min. This step was repeated until the gel became clear. The gel was washed in distiller water, and all solvent was removed. The gel slice was dried by using a speed vac centrifuge for 20 min. Re-swelling the gel piece was carried out by adding 5 µl of 100 mM ABC including 0.05 µg/µl of sequencing grade trypsin, and incubated at 4° C. for 30 min. After twice washing in 25 mM ABC, the digestion was performed by adding a sufficient amount of 25 mM ABC and 10% ACN to cover the gel piece and incubating for 2 hours at 37° C. The supernatant was analyzed by matrix-assisted laser desorption/ionization (MALDI) by using Ultraflex III MALDI-TOF/TOF MS with 'Smartbeam' Laser (Bruker Daltronics).

Figure 2A:
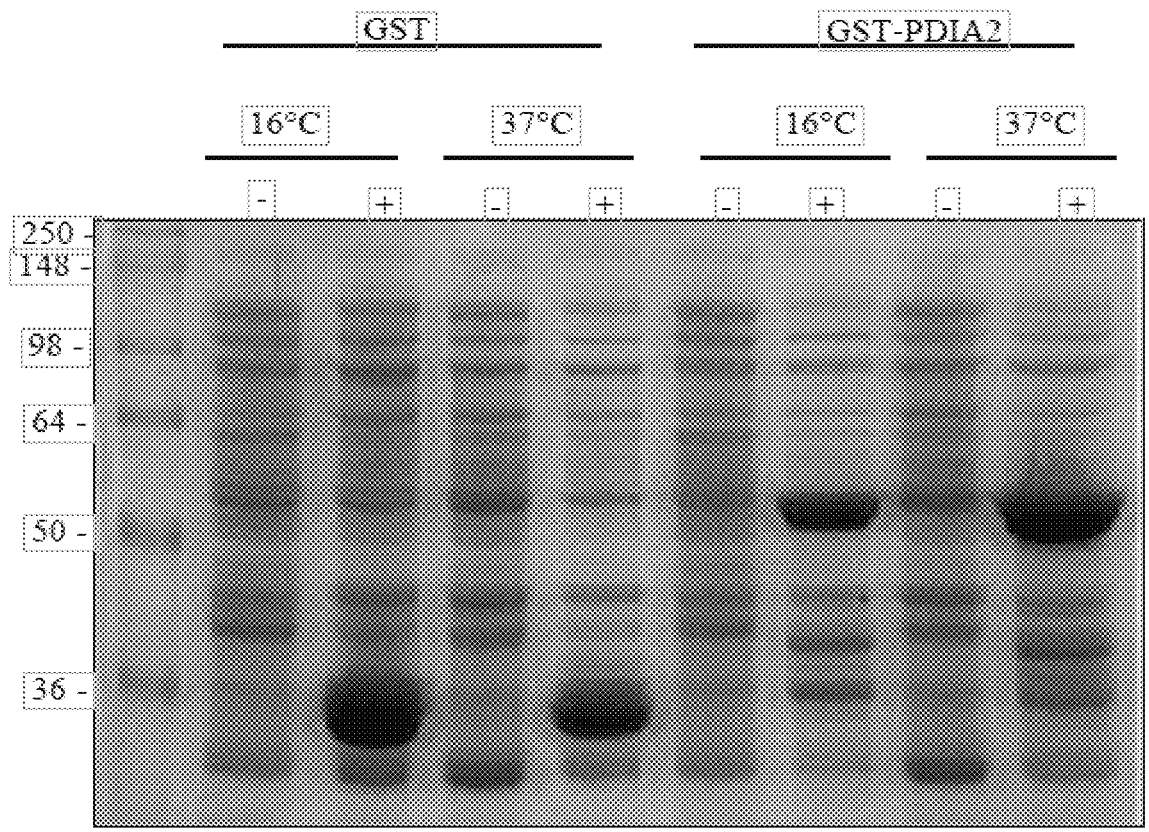
FIG. 2A. Small scale expression of the GST-PDIA2 (504-1024 bp) fragment. Induction with 0.1 mM IPTG (+) at 16° C. and 37° C. produced a 26 kDa band for GST alone as a control and a band of approximately 50 kDa for GST-PDIA2. Uninduced samples (−) were run alongside the induced samples.

Small scale expression of GST-PDIA2. To express protein, the pGEX4T-3 vector and the pGEX4T-3-PDIA2 constructs were transformed into E. coli BL21 codon plus strain. A small scale expression at 16° C. or 37° C. was carried out to select the conditions for a larger scale induction. The GST control was induced by 0.1 mM IPTG overnight (16° C.) or for four hours (37° C.). As shown in FIG. 2A, the induction was successful for the GST control as well as for the PDIA2 fusion protein construct GST-PDIA2. The size of GST control protein is about 26 kDa and the GST-PDIA2 is 47 kDa. These respectively correspond to the marker protein bands around 36 and 50 kDa.

Figure 2B:
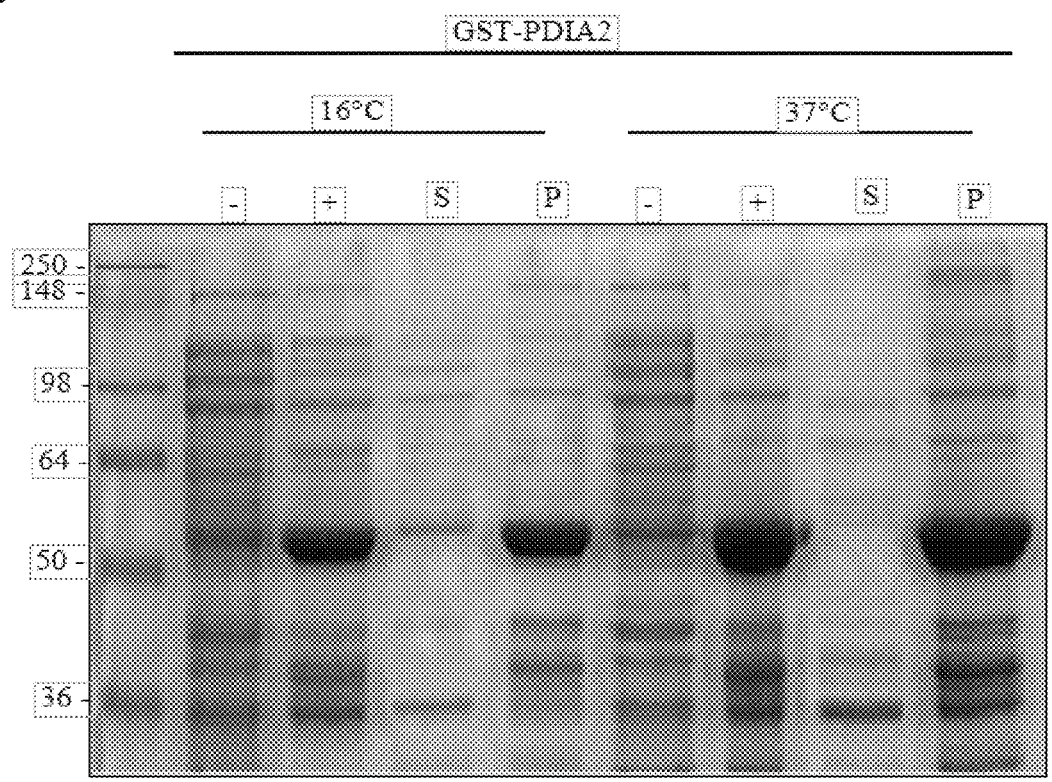
FIG. 2B. Solubility of PDIA2. At 16° C. the majority of GST-PDIA2 at a band of approximately 50 kDa was detected in the insoluble fraction (P) with a faint band in the soluble fraction (S). The cell lysis of GST-PDIA2 at 37° C. produced a band of approximately 50 kDa in the insoluble fraction. No band was detected in the soluble fraction at 37° C. Uninduced samples (−) were run alongside the induced samples.

Solubility at different temperatures and different IPTG concentration. Cells obtained from the small scale expression of GST-PDIA2 at 16° C. or 37° C. were lysed, soluble (S) and insoluble (P) components were separated by centrifugation and samples run on SDS-PAGE. As shown by FIG. 2B, the majority of GST-PDIA2 was observed in the insoluble (P) fraction with a faint band in the soluble fraction expressed at 16° C. using 0.1 mM IPTG. The band was analyzed by mass spectrometry and the result of sequence coverage GST-PDIA2 was 20.3% which indicates the accuracy of expressed protein.

Figure 2C:
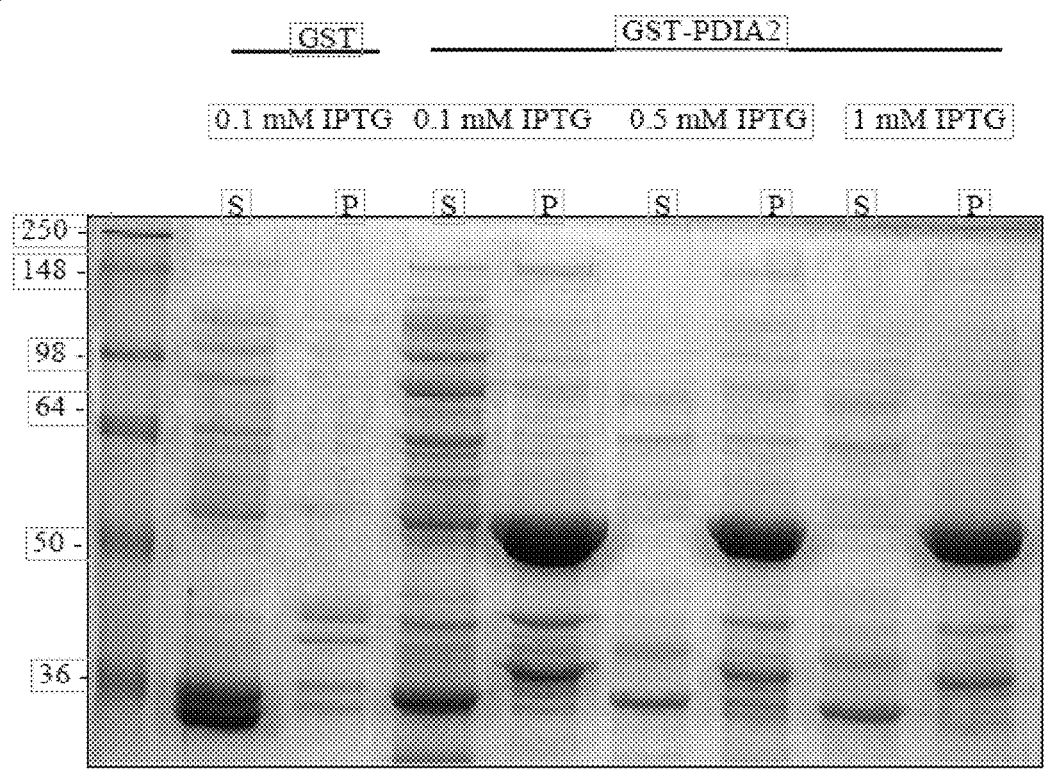
FIG. 2C. Solubility of PDIA2. The expression of GST-PDIA2 at 16° C. produced a band of approximately 50 kDa in the insoluble fraction using 0.5 mM and 1 mM IPTG concentrations. In 0.1 mM IPTG concentration produced a band of approximately 50 kDa in the insoluble fraction with a faint band in soluble fraction. GST alone was induced with 0.1 mM IPTG as a positive control. A band of approximately 26 kDa was detected in the soluble fraction.
Figure 2D:
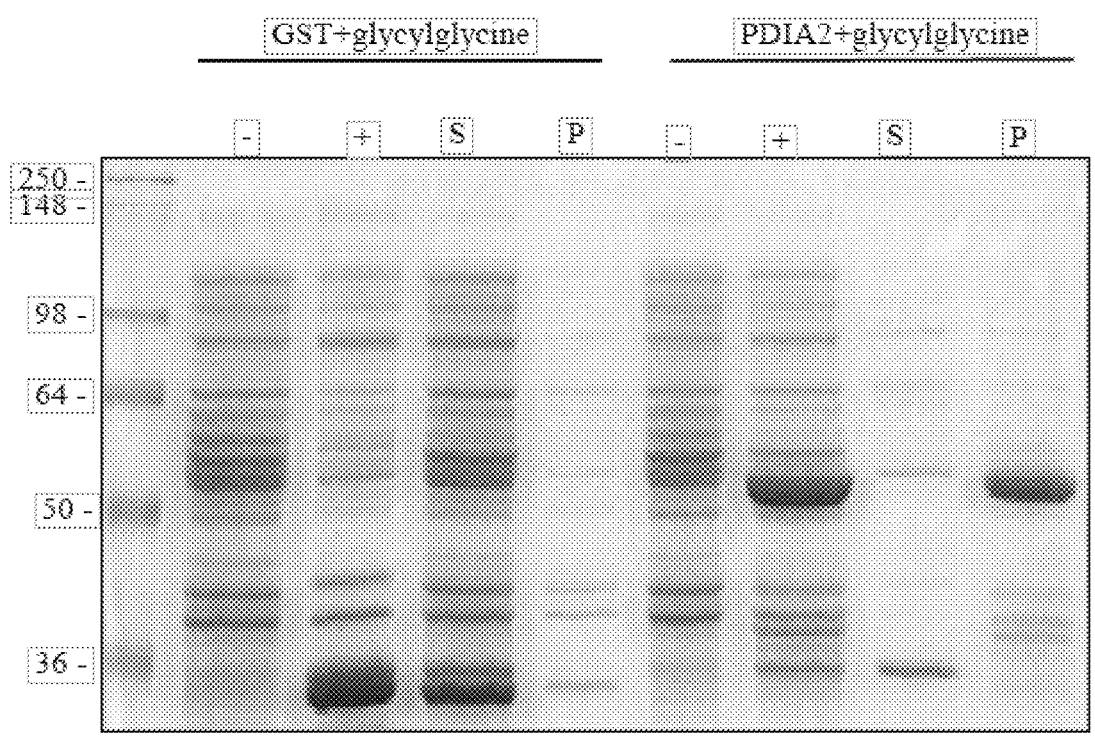
FIG. 2D. Induction and solubility of GST-PDIA2 in the presence of glycylglycine at 16° C. Induction with 0.1 mM IPTG in the presence of glycylglycine at 16° C. produced a 26 kDa band in the soluble fraction (S) for GST as a control and a band of approximately 50 kDa in the insoluble fraction (P) with a faint band in the soluble fraction for GST-PDIA2. Uninduced samples (−) were run alongside the induced samples.

Inducer concentration. FIG. 2C shows the effects on GST-PDIA2 expression of cells induced using IPTG concentrations of 0.1, 0.5, and 1 mM. GST-PDIA2 was recovered in the insoluble (P) fraction and GST control protein in the soluble (S) fraction. Interestingly, an a band of approximately 50 kDa for GST-PDIA2 was observed only in the insoluble fraction after being expressed at 37° C. under all IPTG concentrations and at 16° C. using at the 0.5 mM and 1 mM IPTG concentrations. Surprisingly, this showed that expression of soluble GST-PDIA2 occurred at the lower temperature, but not at the higher 37° C. temperature.

On the basis of the solubility and inducer concentration results the inventor selected induction of GST-PDIA2 at 16° C. using 0.1 mM IPTG.

In view of the lack of, or low solubility of, GST-PDIA2 obtained, other ways of enhancing solubility were evaluated.

Solubility of GST-PDIA2 in the presence of glycylglycine. A small scale induction followed by a solubility test was carried out at 16° C. using 0.1 mM IPTG with glycylglycine. The inventor considers that the presence of glycylglycine in the culture might significantly enhance the solubility GST-PDIA2. For example, Ghosh, et al., Method for enhancing solubility of the expressed recombinant proteins in Escherichia coli (2004) reported that glycylglycine increased the solubility and recovery of recombinant proteins by approximately 170 fold. However, surprisingly, while the GST-PDIA2 construct and GST control protein were well expressed, the GST-PDIA2 band was still observed at approximately 50 kDa in the insoluble fraction with only a faint band in the soluble fraction. Similarly, the GST control protein band was observed at 26 kDa in the soluble fraction. This result was not different to the previous result suggesting the presence of glycylglycine had no influence on the GST-PDIA2 solubility.

Solubility of GST-PDIA2 in different host cell line. The effects of expressing GST-PDIA2 in a different host cell line were evaluated to determine whether host cells that permit formation of disulfide bonds would enhance expression of soluble GST-PDIA2. The GST-PDIA2 construct was transformed into E.coli Shuffle T7 lys Y cell line for protein expression which permits the formation of disulfide bonds in the cytoplasm. This host cell line expresses the disulfide bond isomerase protein DsbC which enhances the correct folding of protein. A small scale induction followed by a solubility test was conducted at 16° C. with different IPTG concentrations of 0.1 mM, 0.5 mM, and 1 mM.

Figure 3:
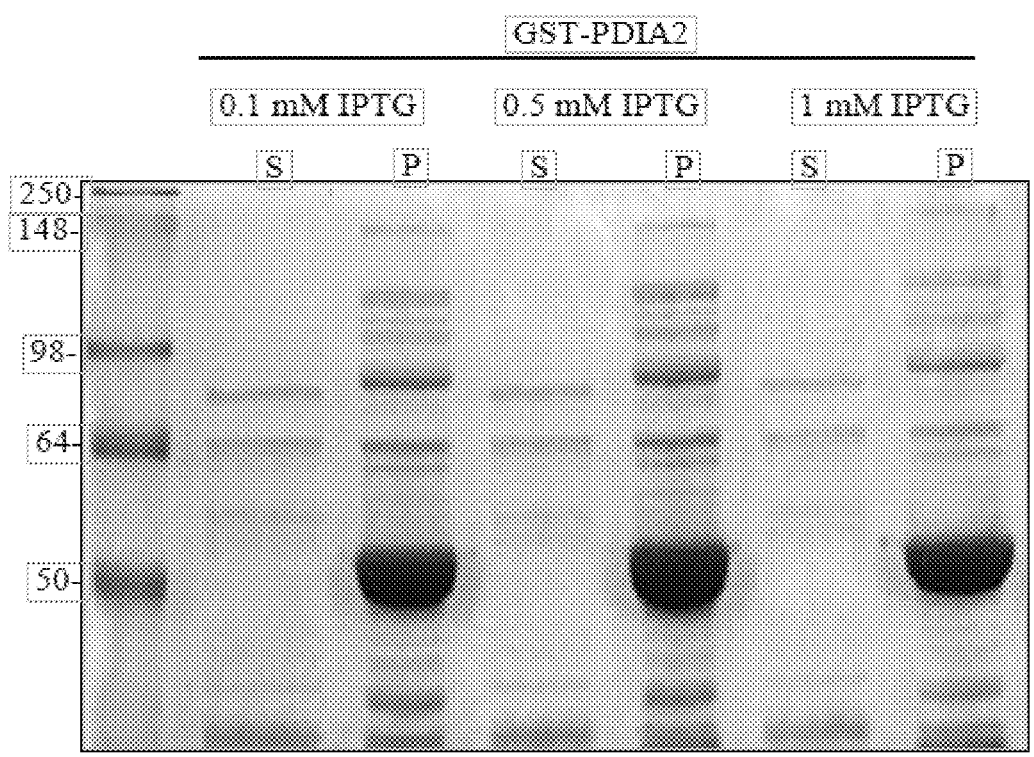
FIG. 3. Solubility of GST-PDIA2 in Shuffle T7 lys Y at 16° C. with different IPTG concentrations. A prominent band at approximately 50 kDa for GST-PDIA2 was observed in the insoluble fractions (P) under 0.1 mM, 0.5 mM and 1 mM IPTG concentrations. No band was observed in any of the soluble fractions (S).

As shown by FIG. 3, a major protein band was observed in the insoluble fraction at the expected size for GST-PDIA2, which is approximately 50 kDa under all IPTG concentrations 0.1 mM, 0.5 mM, and 1 mM. Conversely, no band was observed in the soluble fractions under all IPTG concentrations (0.1 mM, 0.5 mM, 1 mM). In contrast as shown above soluble GST-PDIA2 was expressed by the BL21 codon plus line. Based on these cumulative results, the inventor selected the following conditions to express GST-PDIA2 in a soluble form: induction of expression of GST-PDIA2 in a BL21 codon plus cell line at 16° C. using 0.1 mM IPTG. Based on the results shown above, the inventor scaled up production of GST-PDIA2.

Figure 4A:
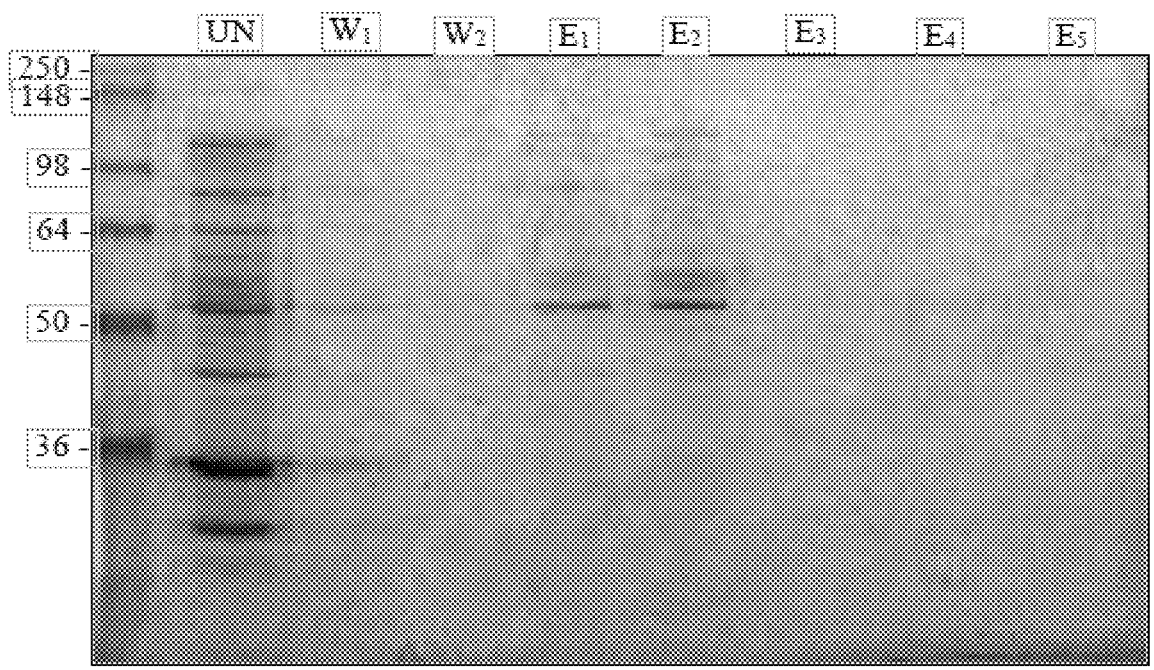
FIG. 4A. Large scale purification of GST-PDIA2. A small amount of purified PDIA2 protein was observed at around a 50 kDa band in elution fractions E1 and E2. Unbound protein fraction (UN) and wash fractions (W1-W2) were also run on the gel.

Large scale purification of GST-PDIA2. 500 ml of culture medium was inoculated with the BL21 codon plus cell line that was transformed to express GST-PDIA2. Induction was carried out at 16° C. using 0.1 mM IPTG in the absence of glycylglycine and the soluble fraction from cell lysis was used for affinity purification of the GST-PDIA2 fusion protein. The soluble fraction obtained from the scaled-up induction and expression of GST-PDIA2 was applied to glutathione sepharose beads which bind to the GST component of GST-PDIA2. Once bound the column was washed and then the bound GST-PDIA2 was eluted. As shown by FIG. 4A, a soluble GST-PDIA2 fusion protein was successfully produced by the scaled-up method as evidenced by a band at the expected size around 50 kDa in elution fractions E1 and E2. While not being bound to any particular theory or explanation the solubility of PDIA2 when induced at 16° C. is consistent with its reduced interaction and entanglement with other cellular proteins at a low temperature, possibly via protein binding sites on the non-catalytic domains of PDIA2.

Figure 4B:
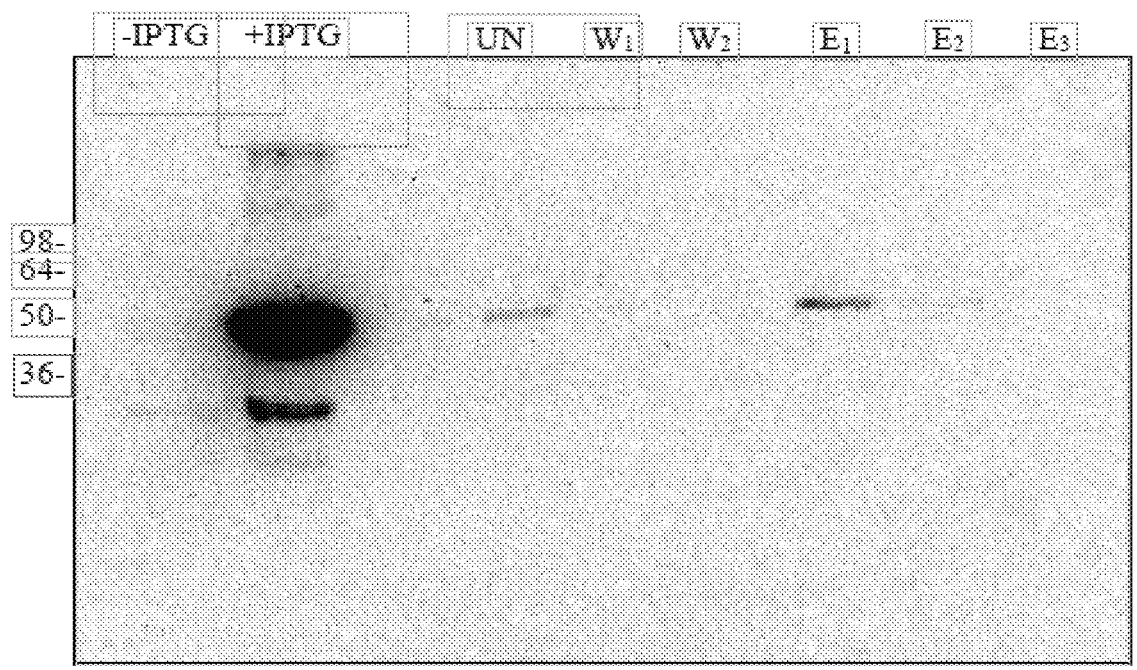
FIG. 4B. Western analysis of GST-PDIA2 purification. The samples were immunoblotted with an anti-GST mouse antibody to detect the presence of GST-PDIA2. A band of approximately 50 kDa for GST-PDIA2 was observed in elution fractions E1and E2. GST-PDIA2 was also detected in the induced sample (+IPTG) and the unbound sample (UN).

Western blot of purified PDIA2. A western blot was performed to confirm the purification of GST-PDIA2 (FIG. 4). Since the construct contained a GST tag, an anti-GST antibody was used to probe the membrane. A band of approximately 50 kDa was detected to confirm the presence of GST-PDIA2 in elution E1 with a faint band in E2 showing that the scaled-up purification of GST-PDIA2 was successful. A prominent band for GST-PDIA2 was detected in the induced fraction (+IPTG) as well as a very faint band in the unbound fraction (UN) suggesting that a very small amount of protein was unbound to the column.

Figure 5:
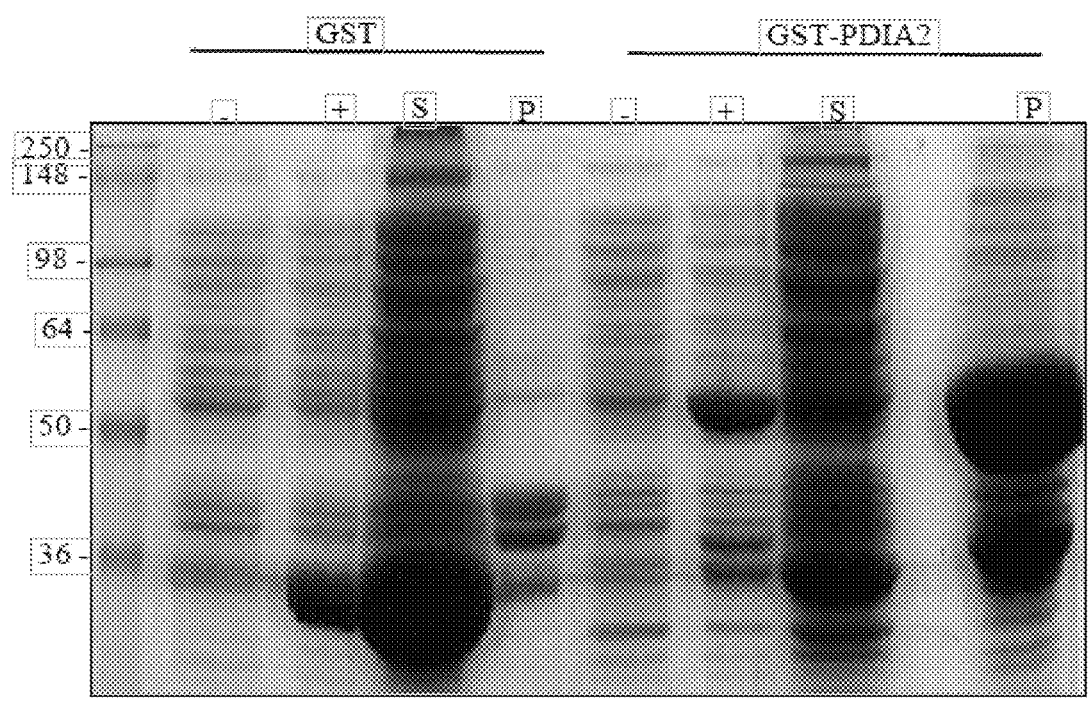
FIG. 5. Large scale expression and solubility of GST-PDIA2. Induction with 0.1 mM IPTG (+) at 16° C. produced a 26 kDa for GST alone as control in the soluble fraction (S). A major protein band was observed at approximately 50 kDa for GST-PDIA2 in the insoluble fraction (P) as well as a small band in the soluble fraction (S). Uninduced fractions (−) were run alongside the induced fractions.

Large scale 4 L expression of soluble GST-PDIA2. A second larger scale induction was conducted with the amount of culture being 4 L but under the same conditions of induction at 16° C. with 0.1 mM IPTG. Induction was successful for the GST-PDIA2 and the GST control protein. After that, cells were lysed and a significant band was observed at 26 kDa for GST as a control in the soluble fraction; FIG. 5.

Many different bands were seen in the soluble fraction after the cell lysis treatment of the GST-PDIA2 construct because of the large amount of culture.

Furthermore, a prominent band was observed in the insoluble fraction at the expected size of GST-PDIA2, which is approximately 50 kDa. A space lane between the soluble and insoluble fractions was required due to the large amount of the culture to avoid the flow through between these fractions.

Figure 6:
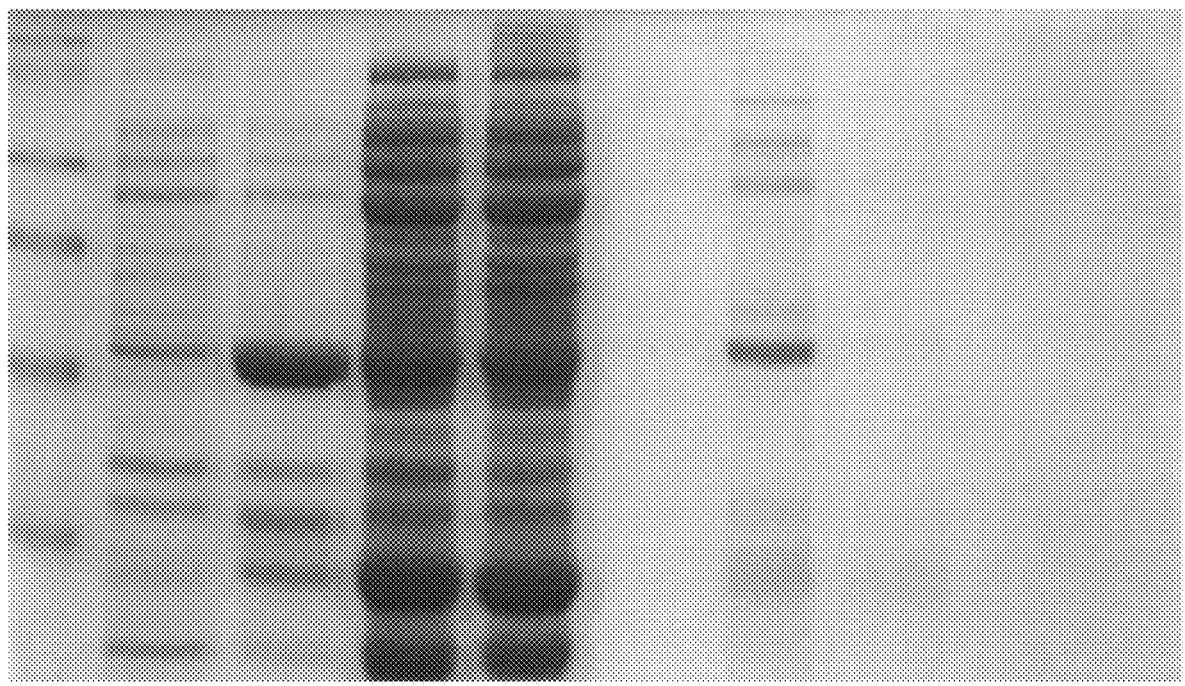
FIG. 6. Large scale purification of GST-PDIA2 (4 L). The pure protein was observed for a band of approximately 50 kDa in elution fraction E1. Uninduced fraction (−), induced fraction (+), soluble fraction (S), unbound fraction (UN) and last wash fraction (W5) were also run on the gel.

Large scale purification of GST-PDIA2. Purification of the GST-PDIA2 fusion protein was performed by using the soluble fraction after cell lysis of large scale expression with the amount of culture being 4 L. As shown by FIG. 6, the GST-PDIA2 was eluted successfully from a glutathione sepharose bead column as evidenced by a prominent band of the expected size for approximately 50 kDa in elution fractions band E1. Many different bands were observed in the soluble fraction and uninduced fraction because of the large amount of culture.

Figure 7:
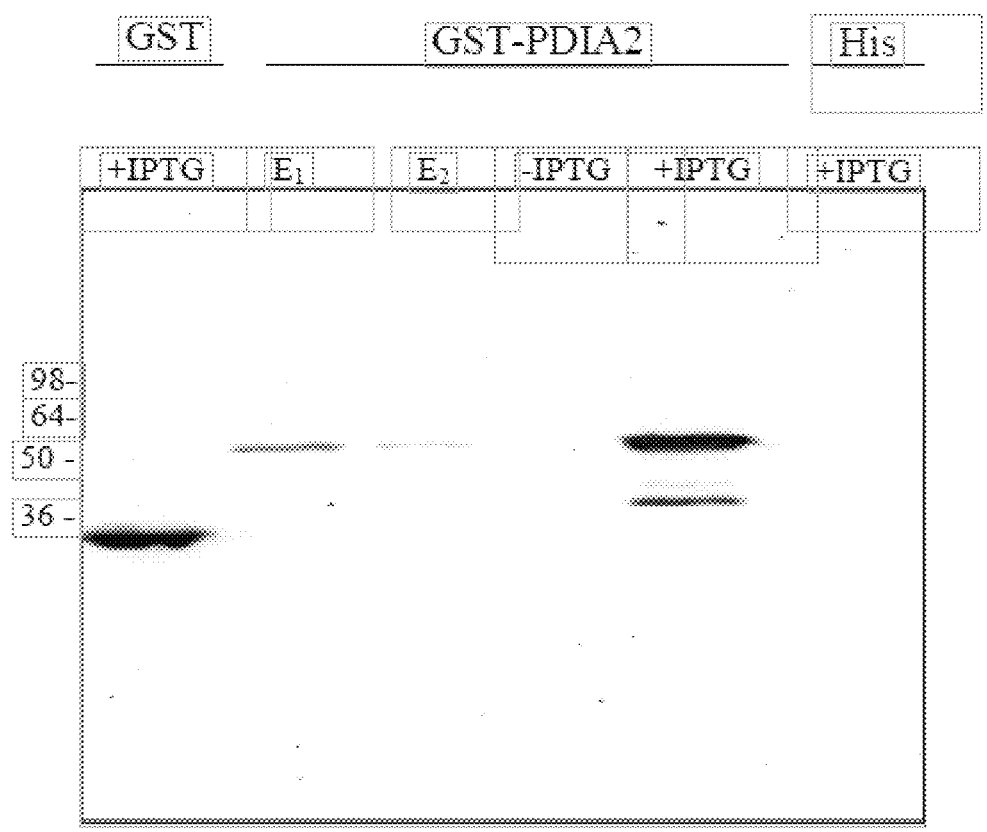
FIG. 7. Western analysis of GST-PDIA2 purification after large scale expression 4 L. The samples were immunoblotted with an anti-GST antibody to detect the presence of GST-PDIA2. A band of approximately 50 kDa for GST-PDIA2 was observed in elution fractions E1 and E2. GST-PDIA2 was also detected in the induced fraction (+IPTG) .Uninduced sample (−IPTG) were run alongside induced sample. An approximate band of a 26 kDa for GST alone as a positive control was detected in the GST induced fraction (+IPTG). No band was observed in the induced fraction (+IPTG) in His-tag protein.

Western blot of purified PDIA2 (4 L). A western blot was performed to confirm the identity of the purified protein. All the samples were transferred on to a nitrocellulose filter (NCF) from a 12% Tris-glycine SDS gel. Since, the fusion protein contained a GST-tag, an anti-GST antibody was utilized to probe the membrane. As shown by FIG. 7, a band of approximately 50 kDa was detected indicting the presence of GST-PDIA2, in the elution fraction E1 with a faint band in E2. Due to the high sensitivity of western blotting, a band in E2 was observed. Hence, the purification of GST-PDIA2 was successful.

A significant band for GST-PDIA2 was also detected in the induced fraction. Moreover, another band was also observed which might be a cleavage product of GST-PDIA2. As a positive control, GST alone was detected at 26 kDa in the GST induced fraction. An unrelated His tagged protein was utilized as a negative control to examine the effectiveness of the anti-GST antibody. A pure soluble protein was obtained.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating damaged tissue comprising contacting the damaged tissue with soluble PDIA2 for a time and under conditions that refold denatured or damaged proteins in the damaged tissue; and
wherein the soluble PDIA2 comprises a glutathione-S-transferase (GST) tag and a segment of PDIA2 having disulphide isomerase activity.

2. The method of claim 1, wherein the damaged tissue includes conjunctiva of an eyelid and the contacting comprises contacting a gelatin-supported PDIA2-containing composition with a damaged surface of the conjunctiva, wherein the damaged surface is a surgical incision.

3. The method of claim 1, wherein the damaged tissue is part of the oral or gastrointestinal lining.

4. The method of claim 1, wherein the damaged tissue is skin.

5. The method of claim 1, wherein the damaged tissue is UV damaged.

6. The method of claim 1, wherein the damaged tissue is damaged by dermatitis.

7. The method of claim 1, wherein the damage tissue has been damaged by over-exposure to estrogen or an estrogen-like compound.

8. The method of claim 1, further comprising:
contacting the damaged tissue with superoxide dismutase and/or an antioxidant.

9. The method of claim 1, wherein said soluble PDIA2 is expressed in *Escherichia coli*.

10. The method of claim 1, wherein said soluble PDIA2 is expressed in *Escherichia coli* that contains extra copies of argU, ileY, and leuW tRNA genes.

11. The method of claim 1, wherein said soluble PDIA2 is expressed by *Escherichia coli* that does not express disulfide bond isomerase protein DsbC.

12. The method of claim 9, wherein expression of the soluble PDIA2 in the *E. coli* is induced by isopropyl β-D-1-thiogalactopyranoside (IPTG).

13. The method of claim 9, wherein the expression of the soluble PDIA2 in the *E. coli* is induced by IPTG at a temperature of no more than 30° C.

14. A method for making soluble PDIA2 comprising:
    inducing expression of a GST-PDIA2 fusion protein, which comprises a glutathione-S-transferase (GST) tag and a segment of PDIA2 having disulphide isomerase activity, in host cells, which contain nucleic acids encoding said fusion protein, at a temperature of no more than 30° C.,
    disrupting the host cells containing the expressed GST-PDIA2 fusion protein;
    separating the disrupted host cells into solid and soluble fraction; and
    recovering GST-PDIA2 fusion protein from the soluble fraction.

15. The method of claim 14, wherein the inducing expression comprises contacting the host cells with isopropyl β-D-1-thiogalactopyranoside (IPTG) at a temperature of no more than 30° C.

16. The method of claim 14, wherein said host cells contain extra copies of argU, ileY, and leuWtRNA genes.

17. The method of claim 14, wherein said disrupting is performed by contacting the induced host cells with lysozyme in the presence of at least one protease inhibitor and in the absence of glycylglycine.

18. A sterile or aseptic composition comprising the soluble PDIA2 made by the method of claim 14 and at least one pharmacological acceptable excipient, humectant, and/or emollient.

19. The method of claim 1, wherein the damaged or denatured tissue comprises eyelid tissue, tissue damaged by blepharoplasty or other surgical techniques used to remove adipose and/or other tissues from underneath the eyelids, or damaged subcutaneous tissue in proximal to the orbicularis oculi or conjunctiva.

20. The method of claim 1, wherein the soluble PDIA2 is made by a method comprising:
    inducing expression of a GST-PDIA2 fusion protein, which comprises a glutathione-S-transferase (GST) tag and a segment of PDIA2 having disulphide isomerase activity, in host cells, which contain nucleic acids encoding said fusion protein, at no more than 30° C.,
    disrupting the host cells containing the expressed GST-PDIA2 fusion protein;
    separating the disrupted host cells into solid and soluble fraction; and
    recovering GST-PDIA2 fusion protein from the soluble fraction.

* * * * *

```
                        SEQUENCE LISTING

<160> NUMBER OF SEQ ID NOS: 5

<210> SEQ ID NO 1
<211> LENGTH: 1578
<212> TYPE: DNA
<213> ORGANISM: Homo sapiens
<220> FEATURE:
<221> NAME/KEY: CDS
<222> LOCATION: (1)..(1578)

<400> SEQUENCE: 1 atg agc cgc cag ctt ctg cct gta ctg ctg ctg ctg ctc agg gct          48
Met Ser Arg Gln Leu Leu Pro Val Leu Leu Leu Leu Leu Arg Ala
1               5                   10                  15 tcg tgc cca tgg ggt cag gaa cag gga gcg agg agc ccc tcg gag gag      96
Ser Cys Pro Trp Gly Gln Glu Gln Gly Ala Arg Ser Pro Ser Glu Glu
                20                  25                  30 cct cca gag gag gaa atc ccc aag gag gat ggg atc ttg gtg ctg agc     144
Pro Pro Glu Glu Glu Ile Pro Lys Glu Asp Gly Ile Leu Val Leu Ser
            35                  40                  45 cgc cac acc ctg ggc ctg gcc ctg cgg gag cac cct gcc ctg ctg gtg     192
Arg His Thr Leu Gly Leu Ala Leu Arg Glu His Pro Ala Leu Leu Val
        50                  55                  60 gaa ttc tat gcc ccg tgg tgt ggg cac tgc cag gcc ctg gcc ccc gag     240
Glu Phe Tyr Ala Pro Trp Cys Gly His Cys Gln Ala Leu Ala Pro Glu
65                  70                  75                  80 tac agc aag gca gct gcc gtg ctc gcg gcc gag tca atg gtg gtc acg     288
Tyr Ser Lys Ala Ala Ala Val Leu Ala Ala Glu Ser Met Val Val Thr
                85                  90                  95 ctg gcc aag gtg gat ggg ccc gcg cag cgc gag ctg gct gag gag ttt     336
Leu Ala Lys Val Asp Gly Pro Ala Gln Arg Glu Leu Ala Glu Glu Phe
            100                 105                 110 ggt gtg acg gag tac cct acg ctc aag ttc ttc cgc aat ggg aac cgc     384
Gly Val Thr Glu Tyr Pro Thr Leu Lys Phe Phe Arg Asn Gly Asn Arg
        115                 120                 125 acg cac ccg gag gag tac aca gga cca cgg gac gct gag ggc att gcc     432
Thr His Pro Glu Glu Tyr Thr Gly Pro Arg Asp Ala Glu Gly Ile Ala
    130                 135                 140 gag tgg ctg cga cgg cgg gtg ggg ccc agt gcc atg cgg ctg gag gac     480
Glu Trp Leu Arg Arg Arg Val Gly Pro Ser Ala Met Arg Leu Glu Asp
145                 150                 155                 160 gag gcg gcc gcc cag gcg ctg atc ggt ggc cgg gac cta gtg gtc att     528
Glu Ala Ala Ala Gln Ala Leu Ile Gly Gly Arg Asp Leu Val Val Ile
                165                 170                 175 ggc ttc ttc cag gac ctg cag gac gag gac gtg gcc acc ttc ttg gcc     576
Gly Phe Phe Gln Asp Leu Gln Asp Glu Asp Val Ala Thr Phe Leu Ala
            180                 185                 190 ttg gcc cag gac gcc ctg gac atg acc ttt ggc ctc aca gac cgg ccg     624
Leu Ala Gln Asp Ala Leu Asp Met Thr Phe Gly Leu Thr Asp Arg Pro
        195                 200                 205 cgg ctc ttt cag cag ttt ggc ctc acc aag gac act gtg gtt ctc ttc     672
Arg Leu Phe Gln Gln Phe Gly Leu Thr Lys Asp Thr Val Val Leu Phe
    210                 215                 220 aag aag ttt gat gag ggg cgg gca gac ttc ccc gtg gac gag gag ctt     720
Lys Lys Phe Asp Glu Gly Arg Ala Asp Phe Pro Val Asp Glu Glu Leu
```

```
                225                 230                 235                 240
ggc ctg gac ctg ggg gat ctg tcg cgc ttc ctg gtc aca cac agc atg      768
Gly Leu Asp Leu Gly Asp Leu Ser Arg Phe Leu Val Thr His Ser Met
                245                 250                 255 cgc ctg gtc acg gag ttc aac agc cag acg tct gcc aag atc ttc gcg      816
Arg Leu Val Thr Glu Phe Asn Ser Gln Thr Ser Ala Lys Ile Phe Ala
        260                 265                 270 gcc agg atc ctc aac cac ctg ctg ttt gtc aac cag acg ctg gct          864
Ala Arg Ile Leu Asn His Leu Leu Phe Val Asn Gln Thr Leu Ala
            275                 280                 285 gcg cac cgg gag ctc cta gcg ggc ttt ggg gag gca gct ccc cgc ttc      912
Ala His Arg Glu Leu Leu Ala Gly Phe Gly Glu Ala Ala Pro Arg Phe
    290                 295                 300 cgg ggg cag gtg ctg ttc gtg gtg gtg gac gtg gcg gcc gac aat gag      960
Arg Gly Gln Val Leu Phe Val Val Val Asp Val Ala Ala Asp Asn Glu
305                 310                 315                 320 cac gtg ctg cag tac ttt gga ctc aag gct gag gca gcc ccc act ctg     1008
His Val Leu Gln Tyr Phe Gly Leu Lys Ala Glu Ala Ala Pro Thr Leu
                325                 330                 335 cgc ttg gtc aac ctt gaa acc act aag aag tat gcg cct gtg gat ggg     1056
Arg Leu Val Asn Leu Glu Thr Thr Lys Lys Tyr Ala Pro Val Asp Gly
            340                 345                 350 ggc cct gtc acc gca gcg tcc atc act gct ttc tgc cat gca gtc ctc     1104
Gly Pro Val Thr Ala Ala Ser Ile Thr Ala Phe Cys His Ala Val Leu
        355                 360                 365 aac ggc caa gtc aag ccc tat ctc ctg agc cag gag ata ccc cct gat     1152
Asn Gly Gln Val Lys Pro Tyr Leu Leu Ser Gln Glu Ile Pro Pro Asp
370                 375                 380 tgg gat cag cgg cca gtt aag acc ctc gtg ggc aag aat ttt gag cag     1200
Trp Asp Gln Arg Pro Val Lys Thr Leu Val Gly Lys Asn Phe Glu Gln
385                 390                 395                 400 gtg gct ttt gac gaa acc aag aat gtg ttt gtc aag ttc tat gcc ccg     1248
Val Ala Phe Asp Glu Thr Lys Asn Val Phe Val Lys Phe Tyr Ala Pro
                405                 410                 415 tgg tgc acc cac tgc aag gag atg gcc cct gcc tgg gag gca ttg gct     1296
Trp Cys Thr His Cys Lys Glu Met Ala Pro Ala Trp Glu Ala Leu Ala
            420                 425                 430 gag aag tac caa gac cac gag gac atc atc att gct gag ctg gat gcc     1344
Glu Lys Tyr Gln Asp His Glu Asp Ile Ile Ile Ala Glu Leu Asp Ala
        435                 440                 445 acg gcc aac gag ctg gat gcc ttc gct gtg cac ggc ttc cct act ctc     1392
Thr Ala Asn Glu Leu Asp Ala Phe Ala Val His Gly Phe Pro Thr Leu
    450                 455                 460 aag tac ttc cca gca ggg cca ggt cgg aag gtg att gaa tac aaa agc     1440
Lys Tyr Phe Pro Ala Gly Pro Gly Arg Lys Val Ile Glu Tyr Lys Ser
465                 470                 475                 480 acc agg gac ctg gag act ttc tcc aag ttc ctg gac aac ggg ggc gtg     1488
Thr Arg Asp Leu Glu Thr Phe Ser Lys Phe Leu Asp Asn Gly Gly Val
                485                 490                 495 ctg ccc acg gag gag ccc ccg gag gag cca gca gcc ccg ttc ccg gag     1536
Leu Pro Thr Glu Glu Pro Pro Glu Glu Pro Ala Ala Pro Phe Pro Glu
            500                 505                 510 cca ccg gcc aac tcc act atg ggg tcc aag gag gaa ctg tag             1578
Pro Pro Ala Asn Ser Thr Met Gly Ser Lys Glu Glu Leu
        515                 520                 525

<210> SEQ ID NO 2
<211> LENGTH: 525
<212> TYPE: PRT
<213> ORGANISM: Homo sapiens
```

```
<400> SEQUENCE: 2

Met Ser Arg Gln Leu Leu Pro Val Leu Leu Leu Leu Arg Ala
1               5                   10                  15

Ser Cys Pro Trp Gly Gln Glu Gln Gly Ala Arg Ser Pro Ser Glu Glu
            20                  25                  30

Pro Pro Glu Glu Glu Ile Pro Lys Glu Asp Gly Ile Leu Val Leu Ser
                35                  40                  45

Arg His Thr Leu Gly Leu Ala Leu Arg Glu His Pro Ala Leu Leu Val
            50                  55                  60

Glu Phe Tyr Ala Pro Trp Cys Gly His Cys Gln Ala Leu Ala Pro Glu
65                  70                  75                  80

Tyr Ser Lys Ala Ala Ala Val Leu Ala Ala Glu Ser Met Val Val Thr
                85                  90                  95

Leu Ala Lys Val Asp Gly Pro Ala Gln Arg Glu Leu Ala Glu Glu Phe
                100                 105                 110

Gly Val Thr Glu Tyr Pro Thr Leu Lys Phe Phe Arg Asn Gly Asn Arg
            115                 120                 125

Thr His Pro Glu Glu Tyr Thr Gly Pro Arg Asp Ala Glu Gly Ile Ala
        130                 135                 140

Glu Trp Leu Arg Arg Arg Val Gly Pro Ser Ala Met Arg Leu Glu Asp
145                 150                 155                 160

Glu Ala Ala Ala Gln Ala Leu Ile Gly Gly Arg Asp Leu Val Val Ile
                165                 170                 175

Gly Phe Phe Gln Asp Leu Gln Asp Glu Asp Val Ala Thr Phe Leu Ala
            180                 185                 190

Leu Ala Gln Asp Ala Leu Asp Met Thr Phe Gly Leu Thr Asp Arg Pro
        195                 200                 205

Arg Leu Phe Gln Gln Phe Gly Leu Thr Lys Asp Thr Val Val Leu Phe
210                 215                 220

Lys Lys Phe Asp Glu Gly Arg Ala Asp Phe Pro Val Asp Glu Glu Leu
225                 230                 235                 240

Gly Leu Asp Leu Gly Asp Leu Ser Arg Phe Leu Val Thr His Ser Met
                245                 250                 255

Arg Leu Val Thr Glu Phe Asn Ser Gln Thr Ser Ala Lys Ile Phe Ala
            260                 265                 270

Ala Arg Ile Leu Asn His Leu Leu Leu Phe Val Asn Gln Thr Leu Ala
        275                 280                 285

Ala His Arg Glu Leu Leu Ala Gly Phe Gly Glu Ala Ala Pro Arg Phe
290                 295                 300

Arg Gly Gln Val Leu Phe Val Val Asp Val Ala Ala Asp Asn Glu
305                 310                 315                 320

His Val Leu Gln Tyr Phe Gly Leu Lys Ala Glu Ala Ala Pro Thr Leu
            325                 330                 335

Arg Leu Val Asn Leu Glu Thr Thr Lys Lys Tyr Ala Pro Val Asp Gly
        340                 345                 350

Gly Pro Val Thr Ala Ala Ser Ile Thr Ala Phe Cys His Ala Val Leu
            355                 360                 365

Asn Gly Gln Val Lys Pro Tyr Leu Leu Ser Gln Glu Ile Pro Pro Asp
        370                 375                 380

Trp Asp Gln Arg Pro Val Lys Thr Leu Val Gly Lys Asn Phe Glu Gln
385                 390                 395                 400

Val Ala Phe Asp Glu Thr Lys Asn Val Phe Val Lys Phe Tyr Ala Pro
```

```
                       405                 410                 415
Trp Cys Thr His Cys Lys Glu Met Ala Pro Ala Trp Glu Ala Leu Ala
                420                 425                 430

Glu Lys Tyr Gln Asp His Glu Asp Ile Ile Ile Ala Glu Leu Asp Ala
            435                 440                 445

Thr Ala Asn Glu Leu Asp Ala Phe Ala Val His Gly Phe Pro Thr Leu
        450                 455                 460

Lys Tyr Phe Pro Ala Gly Pro Gly Arg Lys Val Ile Glu Tyr Lys Ser
465                 470                 475                 480

Thr Arg Asp Leu Glu Thr Phe Ser Lys Phe Leu Asp Asn Gly Gly Val
                485                 490                 495

Leu Pro Thr Glu Glu Pro Pro Glu Glu Pro Ala Ala Pro Phe Pro Glu
                500                 505                 510

Pro Pro Ala Asn Ser Thr Met Gly Ser Lys Glu Glu Leu
            515                 520                 525

<210> SEQ ID NO 3
<211> LENGTH: 10
<212> TYPE: PRT
<213> ORGANISM: Artificial Sequence
<220> FEATURE:
<223> OTHER INFORMATION: Epitope tag

<400> SEQUENCE: 3

Glu Gln Lys Leu Ile Ser Glu Glu Asp Leu
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Epitope tag

<400> SEQUENCE: 4

Tyr Pro Tyr Asp Val Pro Asp Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Epitope tag

<400> SEQUENCE: 5

Asp Tyr Lys Asp Asp Asp Asp Lys
1               5
```